US010049598B1

(12) United States Patent
Langheier et al.

(10) Patent No.: US 10,049,598 B1
(45) Date of Patent: Aug. 14, 2018

(54) PASSIVE TRACKING AND PREDICTION OF FOOD CONSUMPTION

(71) Applicant: Zipongo, Inc., San Francisco, CA (US)

(72) Inventors: Jason Langheier, San Francisco, CA (US); Greg Schwartz, San Francisco, CA (US)

(73) Assignee: Zipongo, Inc., San Francisco, CA (US)

( * ) Notice: Subject to any disclaimer, the term of this patent is extended or adjusted under 35 U.S.C. 154(b) by 284 days.

(21) Appl. No.: 14/514,287

(22) Filed: Oct. 14, 2014

Related U.S. Application Data

(60) Provisional application No. 61/890,179, filed on Oct. 11, 2013.

(51) Int. Cl.
*G09B 19/00* (2006.01)
*G09B 5/00* (2006.01)
(Continued)

(52) U.S. Cl.
CPC ........ *G09B 19/0092* (2013.01); *A61B 5/1118* (2013.01); *A61B 5/4866* (2013.01); *A61B 5/4872* (2013.01); *G09B 5/00* (2013.01)

(58) Field of Classification Search
CPC ................................................ G09B 19/0092
(Continued)

(56) References Cited

U.S. PATENT DOCUMENTS 5,989,188 A * 11/1999 Birkhoelzer ............. A61B 5/00
128/921
2005/0027174 A1* 2/2005 Benardot ............ G06F 19/3487
600/300

(Continued)

FOREIGN PATENT DOCUMENTS

WO WO-2011/143513 A1 11/2011

OTHER PUBLICATIONS

Nayga Jr., Rodolfo M. 'Effects of Socioeconomic and Demographic Factors on Consumption of Selected Food Nutrients.' Oct. 1994. Agricultural and Resource Economics Review. p. 171-182. Accessed Aug. 22, 2016.*
Zipongo, "Quantified Self: Are You What You Eat or What You Buy?," Jan. 27, 2014, two pages, [Online] [Retrieved on Jul. 6, 2015], Retrieved from the internet <URL:https://www.youtube.com/watch?v=H3fMoA3ZSU4>.

*Primary Examiner* — Xuan Thai
*Assistant Examiner* — Kristen Shirley
(74) *Attorney, Agent, or Firm* — Fenwick & West LLP

(57) ABSTRACT

A passive nutrition tracking service automatically tracks food consumption over time for a user and for populations from a variety of food consumption sources, including food purchase input such as grocery loyalty shopping card data, restaurant dining data, estimates of food consumption within a household, estimates of free food intake and estimates of food pantry use. The tracking service also passively tracks and uses total energy expenditure information for the user, which describes the physical activity level, muscle and fat gain, and optionally waste output of the user. The tracking service analyzes the food consumption and user energy expenditure information and generates a food dietary history for the user, which includes calories and nutrient consumption estimated based on the analysis. The tracking service also generates a variety of personalized healthy lifestyle recommendations based on the analysis and presents the dietary history and personalized healthy lifestyle recommendations to the user.

20 Claims, 23 Drawing Sheets

(51) Int. Cl.
*A61B 5/00* (2006.01)
*A61B 5/11* (2006.01)

(58) Field of Classification Search
USPC .......................................................... 434/127
See application file for complete search history.

(56) References Cited

U.S. PATENT DOCUMENTS

| | | | |
|---|---|---|---|
| 2005/0113650 A1* | 5/2005 | Pacione | A61B 5/411 600/300 |
| 2007/0254080 A1* | 11/2007 | Schackmuth | G06Q 10/06 426/523 |
| 2009/0219159 A1* | 9/2009 | Morgenstern | A63B 24/00 340/573.1 |
| 2011/0288378 A1* | 11/2011 | Codd | G06F 19/3431 600/300 |
| 2012/0004972 A1* | 1/2012 | Wengrovitz | G06Q 20/204 705/14.27 |
| 2012/0094258 A1* | 4/2012 | Langheier | G06F 19/3406 434/127 |
| 2013/0157232 A1* | 6/2013 | Ehrenkranz | G01G 19/4146 434/127 |

* cited by examiner

PASSIVE TRACKING AND PREDICTION OF FOOD CONSUMPTION

CROSS REFERENCE TO RELATED APPLICATIONS

This application claims the benefit of U.S. Provisional Application No. 61/890,179, filed Oct. 11, 2013, which is incorporated by reference in its entirety.

BACKGROUND

This invention relates generally to information tracking and processing and particularly to passively and automatically tracking food consumption and nutrient levels (i.e. calories, protein, sodium, etc.) based on food purchases.

Individual tracking of daily diet and exercise is a very useful part of maintaining one's health and nutritional balance. Caloric over-consumption, poor nutritional balance and lack of physical activity are known drivers of negative health outcomes, such as obesity and diabetes, in modernized nations. A common factor in both prevention and treatment of chronic illness is modifying health behavior factors such as nutrition, exercise, tobacco, and alcohol consumption. However, for many individuals, daily diet logging is tedious, and often individuals misreport the amounts and types of food they eat—leading to data that is worse than consistently and passively tracked data that is accurate and used to predict food consumption, such as purchase history.

The recently intensified interest in population health management and development of new technologies has enabled increased adoption of health behavior tracking and planning, such as digital dietary logging and activity tracking. However, existing solutions of health behavior tracking and planning do not allow users quantitatively, accurately and consistently track their dietary intake in a user friendly way and the existing solutions often require continuous active tracking activities from the users. For example, conventional self-report food frequency questionnaires are known for being imprecise. Conventional food journals are accurate only when food items are tracked at the time of consumption, but very few people typically take the time and effort to provide this level of details about what they eat, for more than a period of a couple of weeks; food journaling performs poorly in populations.

SUMMARY

Embodiments of the invention provide a solution to automatic and accurate nutrition tracking and prediction of energy intake and levels of key nutrients of individuals, households and populations based on user food consumption, over time. The solution is based on passive dietary tracking that automates calories and nutrient prediction primarily from purchase input received from user grocery and restaurant purchase and user physical activities. The passive tracking of user food consumption is beneficial to the entire population in proving health behavior change programs. Reducing or eliminating the burden of lifestyle tracking has great potential to expend the reach and effectiveness of self-monitoring, behavior change programs and disease prevention and treatment.

The solution comprises a passive nutrition tracking service that passively tracks food consumption for a user from a variety of food consumption sources, including food purchase input such as grocery loyalty shopping card data, restaurant dining data, estimates of food consumption within a household, estimates of free food intake and estimates of food pantry use. The tracking service also passively tracks energy expenditure information for the user, which describes the physical activity level, muscle and fat gain, and optionally waste output of the user. The tracking service analyzes the food consumption and user energy expenditure information and generates a food dietary history for the user, which includes calories and nutrients consumption estimated based on the analysis. The tracking service also generates a variety of personalized healthy lifestyle recommendations based on the analysis and presents the dietary history and personalized healthy lifestyle recommendations to the user in a user friendly way.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

System Overview

A solution is provided to automate accurate tracking of calories and nutrients by passively tracking user food purchases, energy expenditure and other calories and nutrients contributors. In this disclosure, "passive tracking," "passive nutrition tracking" or "passive food consumption tracking" generally refers to any tracking of food purchases and consumption without user active subsequent tracking activities after an initial tracking setup. Taking passive nutrition tracking based on a user's grocery purchases as an example, the initial tracking setup allows the user to register his/her grocery loyalty shopping card, e.g., SAFEWAY™ reward card, with a passive tracking service, such as passive nutrition tracking service 130 of FIG. 1 described below. Taking another example of passive nutrition tracking based on a user's dining in restaurants, the initial tracking setup allows the user to integrate data from his/her credit cards used at restaurants, e.g., such as syncing their MINT.COM™ credit card and banking tracking service, with the passive nutrition tracking service 130. The initial registration of the user's grocery loyalty card or restaurant credit card eliminates the subsequent user active tracking activities, such as manually reporting each of the individual foods the user buys or eats each day. The passive nutrition service 130 gets a reliable and automatic ongoing feed of information, such as purchase history, and purchase nutrient history, every time a user purchases food using his/her grocery loyalty card or pays for the food at a restaurant. Food purchase item vocabularies for food venues are stored and matched to a user food history, and matched with nutrients in the database.

Figure 1:
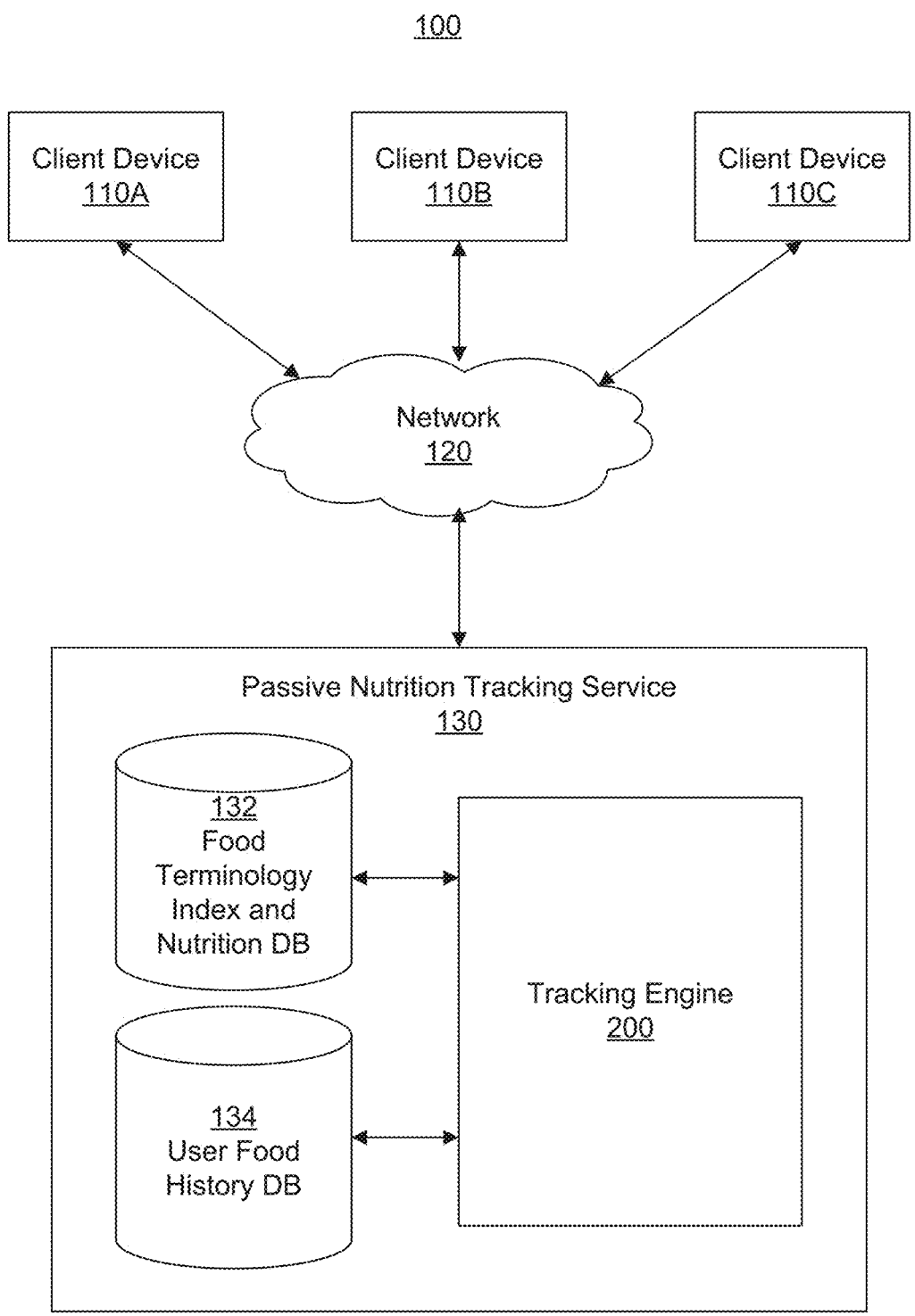
FIG. 1 is a block diagram of a computing environment for passive nutrition tracking according to one embodiment.

FIG. 1 is a block diagram of a computing environment 100 for passive nutrition tracking according to one embodiment. The embodiment illustrated in FIG. 1 includes three client devices, 110A, 110B and 110C, and a passive nutrition tracking service 130 connected to each other by a network 120. Only three client devices 110 and one a passive nutrition tracking service 130 are shown in FIG. 1 in order to simplify and clarify the description. Embodiments of the computing environment 100 can have many client devices 110 and passive nutrition tracking services 130 connected to the network 120. Likewise, the functions performed by the various entities of FIG. 1 may differ in different embodiments.

A client device 110 is an electronic device used by a user to perform functions such as executing software applications, browsing websites hosted by web servers on the network 120, uploading and downloading files and the like. For example, the client device 110 may be a smart phone, a tablet, notebook, or desktop computer. The client device 110 includes and/or interfaces with a display device on which the user may view webpages, videos and other digital content. In addition, the client device 110 may include an image capture device, such as a digital camera, for capturing an image of a meal, and a global position system (GPS) for determining the location of the client device 110. Furthermore, the client device 110 provides a user interface (UI), such as physical and/or on-screen buttons, with which the user may interact with the client device 110 to perform functions such as capturing a digital image of an object, scanning a text page, selecting, and consuming digital content such as healthy lifestyle blogs.

In another embodiment, the client device 110 is a wearable electronic device for passively tracking user physical activities. For example, the wearable electronic device has a built-in accelerometer and is worn by a user on his/her wrist, in clothing or shoes to measure his/her movement. Other embodiments of the client device 110 include personal health management tools, such as a wireless-based scale that sends weight and body fat percentage information over the Internet to a receiving computing device (e.g., the passive nutrition tracking service 130).

The client devices 110 are configured to communicate with the passive nutrition tracking service 130 and among each other via the network 120, which may comprise any combination of voice and data networks, using both wired and wireless communication systems and in one embodiment includes the Internet. In one embodiment, the network 120 uses standard communications technologies and/or protocols. Thus, the network 120 may include links using technologies such as public switched telephone network (PSTN), Ethernet, 802.11, worldwide interoperability for microwave access (WiMAX), 3G, 4G, code division multiple access (CDMA), digital subscriber line (DSL), etc. Similarly, the networking protocols used on the network 120 may include multiprotocol label switching (MPLS), transmission control protocol/Internet protocol (TCP/IP), User Datagram Protocol (UDP), hypertext transport protocol (HTTP), simple mail transfer protocol (SMTP) and file transfer protocol (FTP). Data exchanged over the network 120 may be represented using technologies and/or formats including hypertext markup language (HTML) or extensible markup language (XML). In addition, all or some of links can be encrypted using conventional encryption technologies such as secure sockets layer (SSL), transport layer security (TLS), and Internet Protocol security (IPsec).

The passive nutrition tracking service 130 passively tracks food consumption for a user from a variety of food consumption sources, including food purchase input such as grocery loyalty shopping card data, restaurant dining data, estimates of food consumption within a household, estimates of free food intake and estimates of food pantry use. The passive nutrition tracking service 130 also passively tracks calorie usage (or energy expenditure) information for the user via any of a number of sources, such as an integrated physical activity trackers to assess physical activity, or embedded scales to assess weight (muscle, water and fat) gain; waste output of the user can be tracked by toilets that track waste weight. Any of these energy expenditure items can be self-reported, and any missing data can be estimated by the passive tracking system based on stored population norms, refined over time as more users use the system. The energy expenditure information enables the passive nutrition tracking service 130 to derive calories burned by the user due to physical exercise, muscle and fat gain, and optionally waste output of the user. By definition, the calories consumed must equal total calorie usage (energy expenditure), as just described. Thus, the energy expenditure information is used by the passive tracking service to estimate the calories consumed. This information is then used by the passive tracking service as a reference point to initially estimate the intake of all other nutrients. The proportion of foods purchased and then averaged over a three month period back to a daily intake level, are held equal, and then adjusted to match the calorie intake estimated by the total energy expenditure, by the passive tracking service. The passive nutrition tracking service 130 further adjusts the estimations based on any available prior self-report tracking history, food frequency questionnaire data and household demographic data revealing the likely consumption habits based on age and sex of household members. The passive nutrition tracking service 130 also generates a variety of personalized healthy lifestyle recommendations based on the analysis and presents the dietary history and personalized healthy lifestyle recommendations to the user in a user friendly way.

In one embodiment, the passive nutrition tracking service 130 includes a food terminology index and nutrition database 132, a user food history database 134 and a tracking engine 200. Those of skill in the art will recognize that other embodiments of the passive nutrition tracking service 130 can have different and/or other modules than the ones described here, and that the functionalities can be distributed among the modules in a different manner.

The food terminology index and nutrition database 132 stores indices for various types of food and nutrients associated with each type of good. In one embodiment, the food terminology index and nutrition database 132 contains multiple tables and relationship references to each type of food and its associated nutrients. For example, a table for a particular food contains information describing the food in terms of food name/identification, food type, subtypes, cooking method, preparation method, storage method, derivative nutrient interpretations (e.g., low sodium, high fat, etc.), food manufacture, linked retail venues, farm source and location and ingredients.

Each food table links to a corresponding nutrients table that lists the nutrients for the identified food. Each food indexed in the database 132 may also links to a normalized recipe table for the identified food. Each food may further has derivative tags that note allergens, vegetarian status, food status prepared in accordance with a particular religious dietary law, e.g., Kosher status for food prepared in accordance with Jewish dietary laws, and other food restrictions. In one embodiment, the food tables and nutrients tables are generated by the passive nutrition tracking service 130 based on the United States Department of Agriculture National Nutrient Database for Standard Reference, the National Health and Nutrition Examination Survey (NHANES) statistics from the Centers for Disease Control and Prevention (CDC) of the United States (the NHANES statistics track key population-level diet and consumption measures), and grocer transaction system and restaurant point of sale menu data previously collected.

A user food history database 134 stores food purchase input and user energy expenditure information. In one embodiment, the user food history database 134 stores food purchase input, such as grocery and restaurant purchases linked to user's grocery loyalty cards and restaurant credit cards. The user food history database 134 also stores user energy expenditure information based on user physical activity, weight changes, food waste and food spoilage passively tracked by the client device 110, such as the wearable electronic device having a built-in accelerometer for movement measurement and the wireless-based scale for weight and body fat percentage information.

The user food history database 134 also stores user profiles, each of which includes a user identification and demographic and genetic information, such as race, gender, age and genetic mutations that may affect metabolism of certain nutrients. A user profile is associated with one or more food tables and the corresponding nutrients tables. A user profile is updated upon food purchase input and user energy expenditure information associated with the identified user. In one embodiment, the user food history database 134 is partitioned into subsections for storing food purchase input, user energy expenditure information and user profiles separately.

The passive nutrition tracking service 130 may also include an activity database (not shown in FIG. 1), which creates a hierarchy of user physical activities. Exemplary data linked to each type of activity can include activity type, activity subtype, rate of caloric expenditure related to intensity and duration of an activity, required equipment environment for performing the activity and ancillary gear used for the activity. The rate of caloric expenditure also links to classifications of activities related to their primary physical benefits, such as aerobic, cardiovascular, strength, speed and flexibility. The passive nutrition tracking service 130 uses the activity database to correlate estimation of calories consumption and nutrients intake based on passive nutrition tracking further described below.

The tracking engine 200 passively tracks food consumption from a variety of food consumption sources and energy expenditure information for a user, generates a comprehensive and accurate user food dietary history and personalized healthy lifestyle recommendations to the user and presents the food dietary history and personalized healthy lifestyle recommendations to the user in a user friendly way. The tracking engine 200 is further described with reference to FIG. 2, FIG. 3 and FIG. 4 below.

Passive Nutrition Tracking

Figure 2:
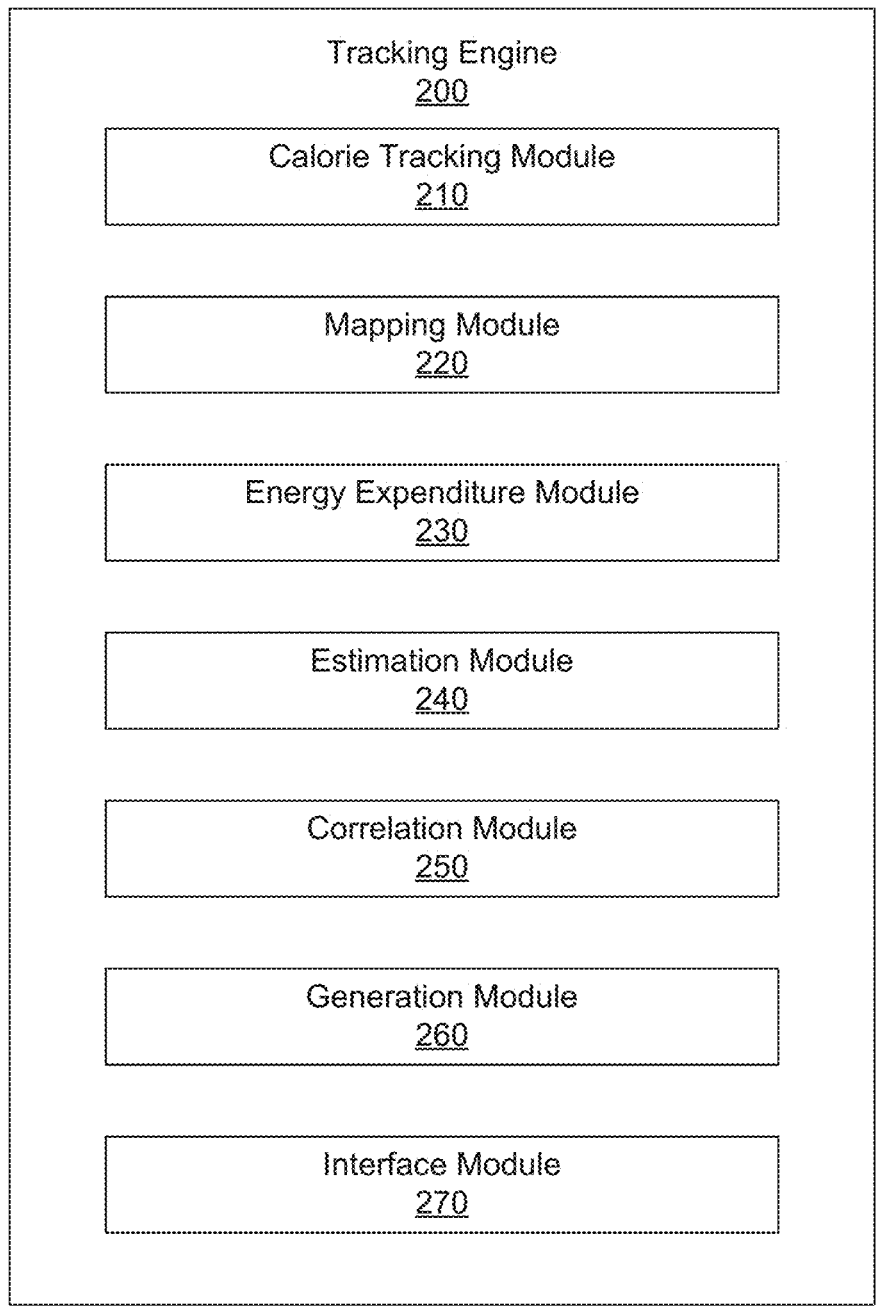
FIG. 2 illustrates an example of a tracking engine according to one embodiment.

FIG. 2 illustrates an example of a tracking engine 200 of the passive nutrition tracking service 130 illustrated in FIG. 1 according to one embodiment. In one embodiment, the tracking engine 200 includes a calorie tracking module 210, a mapping module 220, an energy expenditure module 230, an estimation module 240, a correlation module 250, a generation module 260 and an interface module 270.

Figure 5:
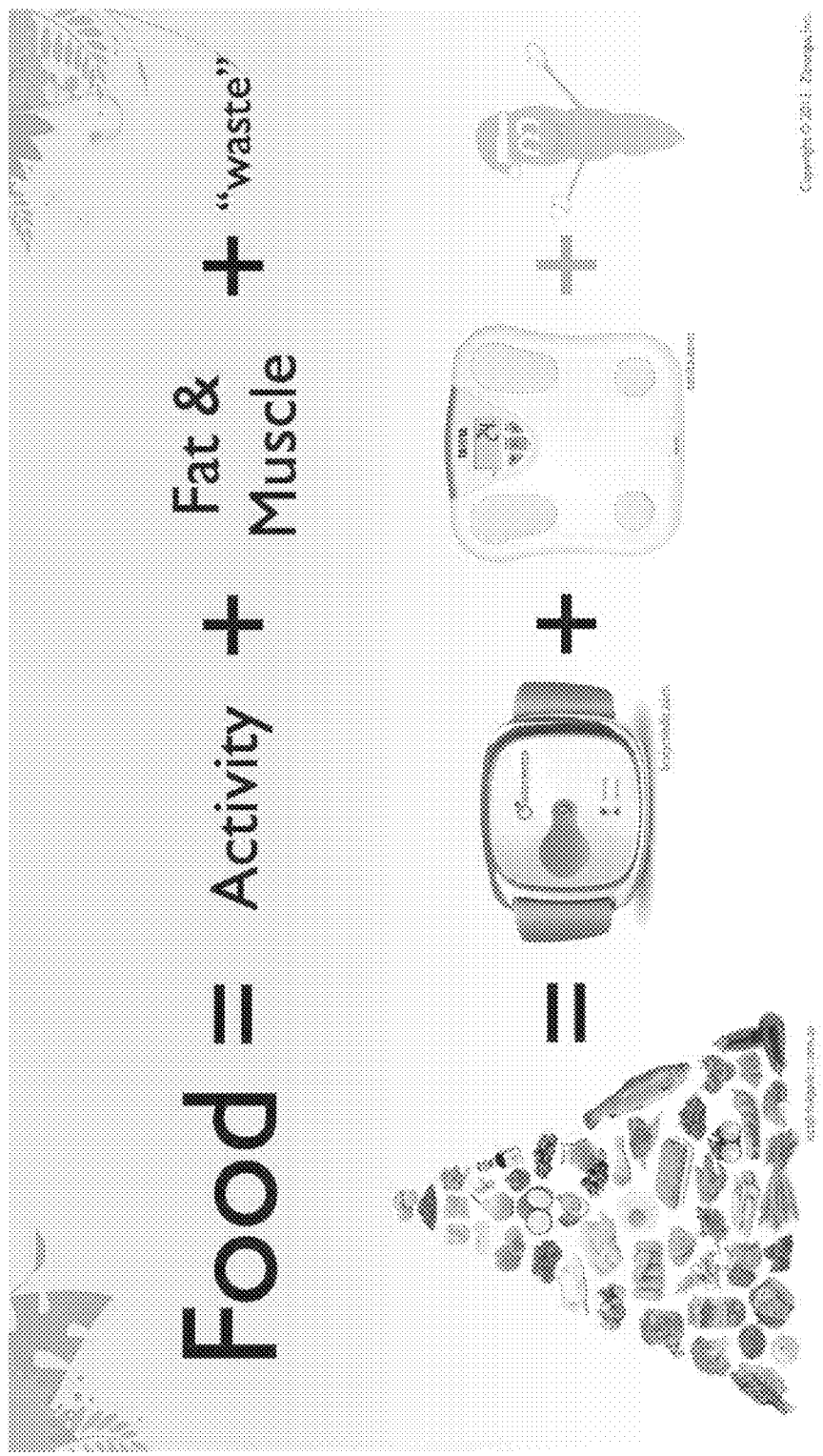
FIG. 5 illustrates a relationship between total calories (one example nutrient) from food consumed by a user and total calories based on the user's energy expenditure.

Ideally, the total calories of a user's food consumption should approximate the total calories consumed by the user's energy expenditure represented by user physical activities, muscle and fat gain and optionally waste output. FIG. 5 illustrates a relationship between total calories from food consumed by a user and total calories based on the user's energy expenditure represented by physical activities, muscle and fat gain and optionally waste output. In other words, the body of the user in this context functions as a calorie converter: food consumed by the user gets transformed into energy for physical activity, muscle and fat gain and waste. However, the ideal approximation between the total calories of a user's food consumption and the total calories consumed by the user's energy expenditure depends largely on accurate tracking of the user's actual food consumption.

Figure 7:
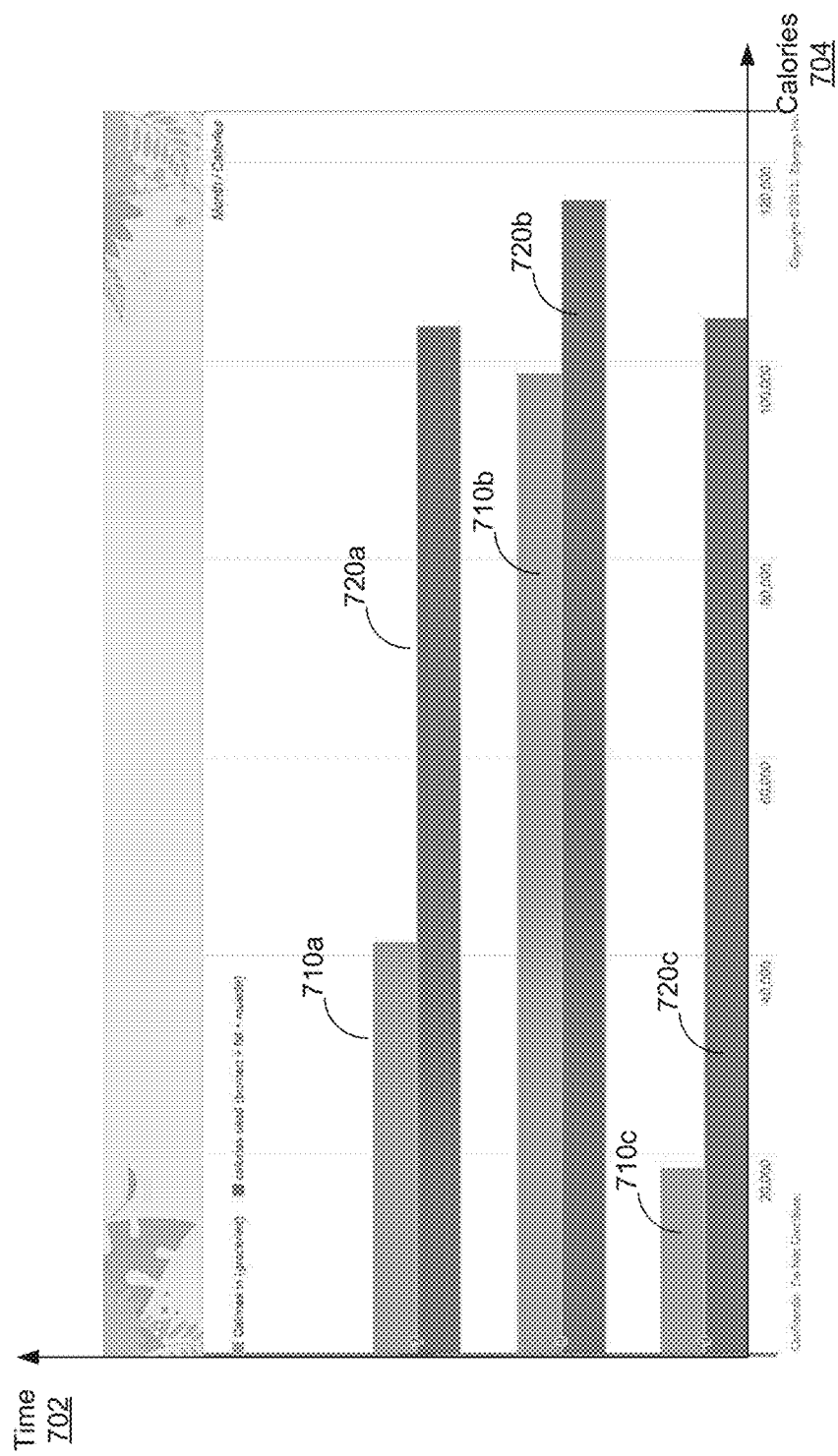
FIG. 7 shows examples of discrepancies between calories estimated based on nutrition tracking of user grocery purchases and calories based on the user's energy expenditure.

There are various factors that can contribute to total calories and nutrients of food consumption by a user, such as restaurant dining and free food catered at work or consumed at a friend's house. Tracking food consumption solely based on the grocery purchases often misreports the actual food consumption of the user. FIG. 7 shows examples of discrepancies between calories estimated based on nutrition tracking from user grocery purchases and calories based on the user's energy expenditure. The examples shown in FIG. 7 include calories from food consumption of a user, 710a, 710b, 710c, tracked based on the user's grocery purchase data, e.g., purchasing data linked to the user's SAFEWAY™ reward card, over a period of three months. The corresponding user's energy expenditure over the same period of time are measured by physical activity, muscle and fat gain, 720a, 720b, 720c, respectively, via integrated devices, self-report or estimation based on population norms. The examples in FIG. 7 show large discrepancy between the calories based on the tracked food consumption and the calories based on the energy expenditure, especially during the first and last month of the tracking period.

Figure 3:
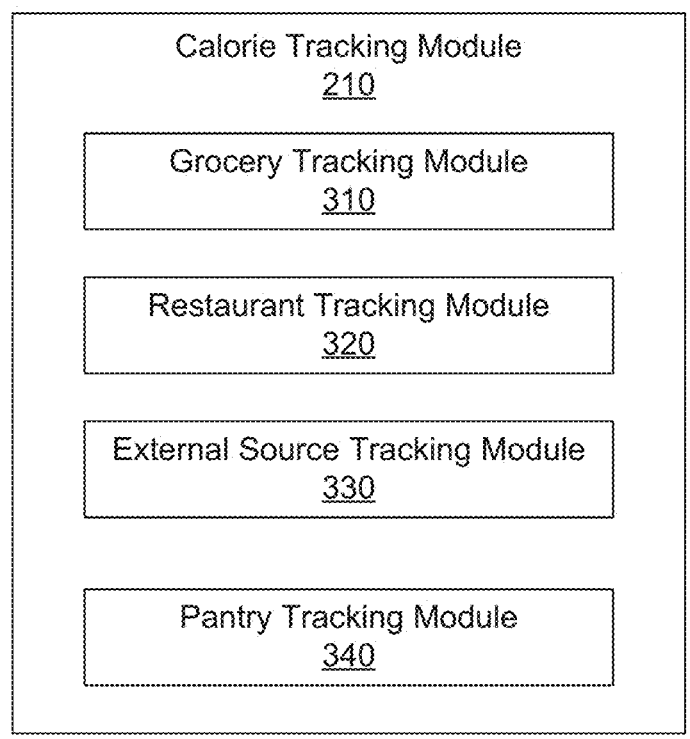
FIG. 3 is a block diagram of an exemplary calorie tracking module according to one embodiment.

To more accurately track food consumption of a user, the calorie tracking module 210 passively tracks food consumption for a user from a variety of food consumption sources, including food purchase input, e.g., grocery loyalty shopping card data, restaurant credit card and point of sale purchase data, estimates of food consumption within a household, estimates of free food intake and estimates of food pantry use. Referring now to FIG. 3, FIG. 3 is a block diagram of an exemplary calorie tracking module 210 according to one embodiment. The calorie and nutrient tracking module 210 shown in FIG. 3 includes a grocery tracking module 310, a restaurant tracking module 320, an external source tracking module 330 and a pantry tracking module 340.

In one embodiment, the grocery tracking module 310 passively and automatically tracks food consumption based on food purchase input from grocery loyalty shopping card data. The grocery tracking 210 registers a user's grocery loyalty shopping card once with the passive nutrition tracking service 130 and continues to receive food purchase data associated with the user upon each of user grocery purchases from a computer server that processes the user grocery purchases, such as a SAFEWAY™ computer server. For example, the grocery tracking module 310 currently receives food purchase data from approximately 25,000 grocery stores, primarily large grocery and pharmacy chains. The grocer tracking module 310 stores the received data in the user food history database 134 of the passive nutrition tracking service 130 for further processing.

The restaurant tracking module 320 passively and automatically tracks food consumption based on food purchase input from restaurant credit card and point of sale purchase data. The restaurant tracking module 320 registers a user's restaurant dining card or a regular credit card once with the passive nutrition tracking service 130 and continues to receive food purchase data associated with the user upon each of user restaurant purchases from a computer server that processes the user restaurant purchases, such as a credit card data on the MINT.COM™ computer servers, transmitted by the passive tracking services integration with the MINT.COM application programming interface (API). The restaurant tracking module 320 stores the received data in the user food history database 134 of the passive nutrition tracking service 130 for further processing, matching menu names to the previously mentioned food terminology index, to estimate the calories and nutrient levels of each item purchased.

The external source tracking module 330 passively and automatically tracks food consumption based on other food consumption contributors, such as amount of free food consumed by the user. Examples of free food are food catered at work or food eaten at a friend's home. The external source tracking module 330 receives supplementary food consumption from the user through a variety of methods, such as manual entries. The external source tracking module 330 also augments the food consumption by eliminating possible factors that are not contributing to the user's food consumption, such as amount of food shared by other members within the household of the user.

Figure 6:
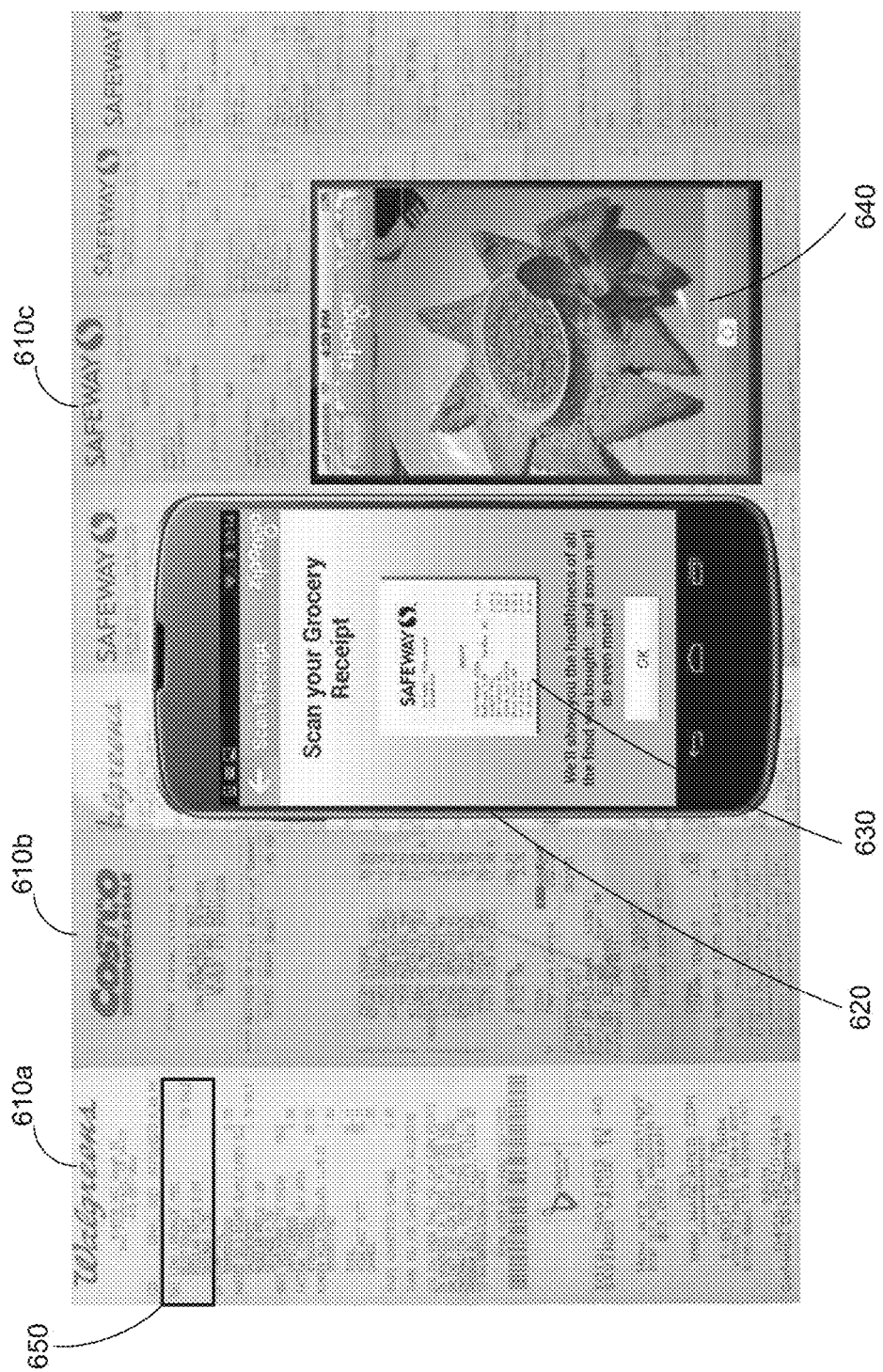
FIG. 6 shows examples of passive nutrition tracking based on input received from a scanned user grocery purchase receipt and a captured image of a restaurant dish consumed by a user.

FIG. 6 shows examples of passive nutrition tracking based on input received from a scanned user grocery purchase receipt and a captured image of a restaurant dish consumed by a user. The examples shown in FIG. 6 show the user's grocery purchases from various grocery and pharmacy stores, e.g., WALGREENS™, SAFEWAY™ and WINN-DIXIE™. The user can also use his/her smart phone 620 to scan a purchase receipt 630 or, to supplement passive tracking, actively take a picture of the dish 640 he/she purchased from a restaurant. The external source tracking module 330 receives the scanned purchase receipt 630 and the picture of the dish 640 from the smart phone 620 and stores the received data in the user food history database 134 of the passive nutrition tracking service 130 for further processing.

Figure 10:
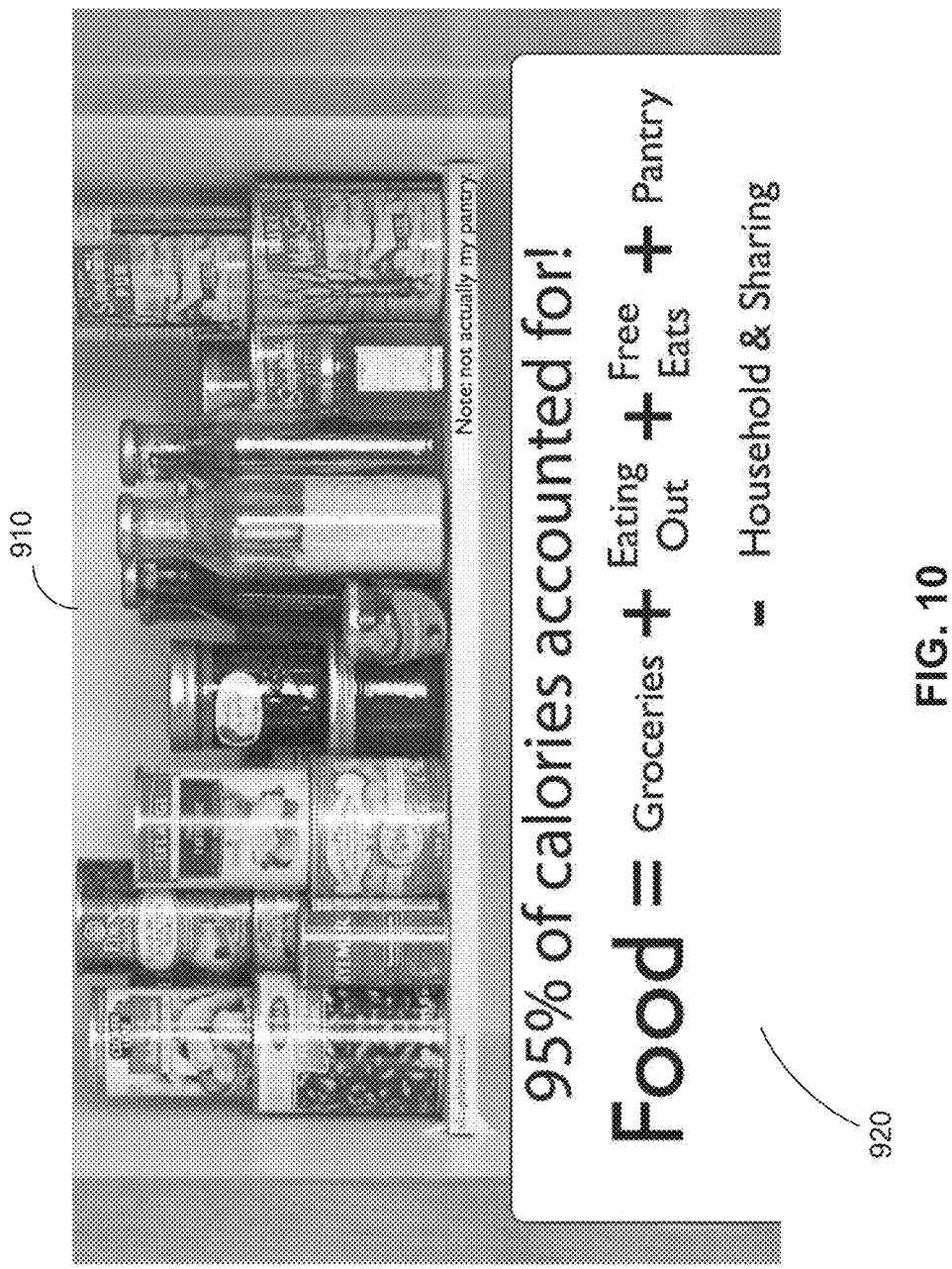
FIG. 10 shows an example of passive nutrition tracking that accounts for calories and nutrients contributed by a user's household pantry items.

The pantry tracking module 340 passively and automatically tracks food consumption based on food pantry usage associated with a user, based on camera images of the user's pantry, or baseline self-reporting about what is contained in one's pantry. In one embodiment, the pantry tracking module 340 uses normalized society data, such as average pantry food consumption based on survey data of a controlled group of population. The pantry tracking module 340 may further personalize the food consumption tracking based on user input, e.g., family size and pantry inventory. The pantry tracking module 340 stores the received data in the user food history database 134 of the passive nutrition tracking service 130. FIG. 10 shows an example of passive nutrition tracking that accounts for calories and nutrients contributed by a user's household pantry items 910.

Figure 8:
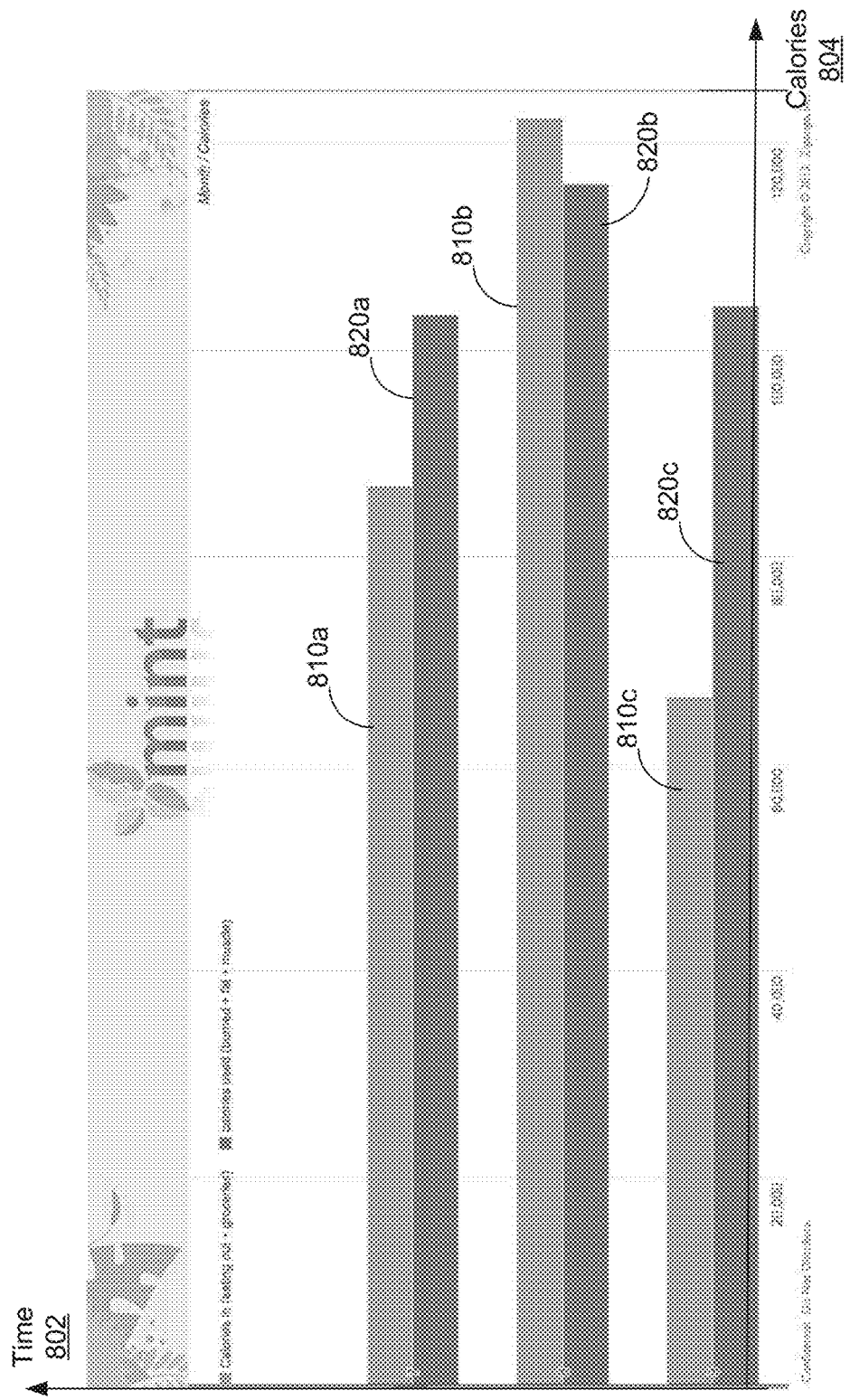
FIG. 8 shows examples of increased accuracy of nutrition tracking based on both user grocery purchase data and restaurant purchase data.
Figure 9:
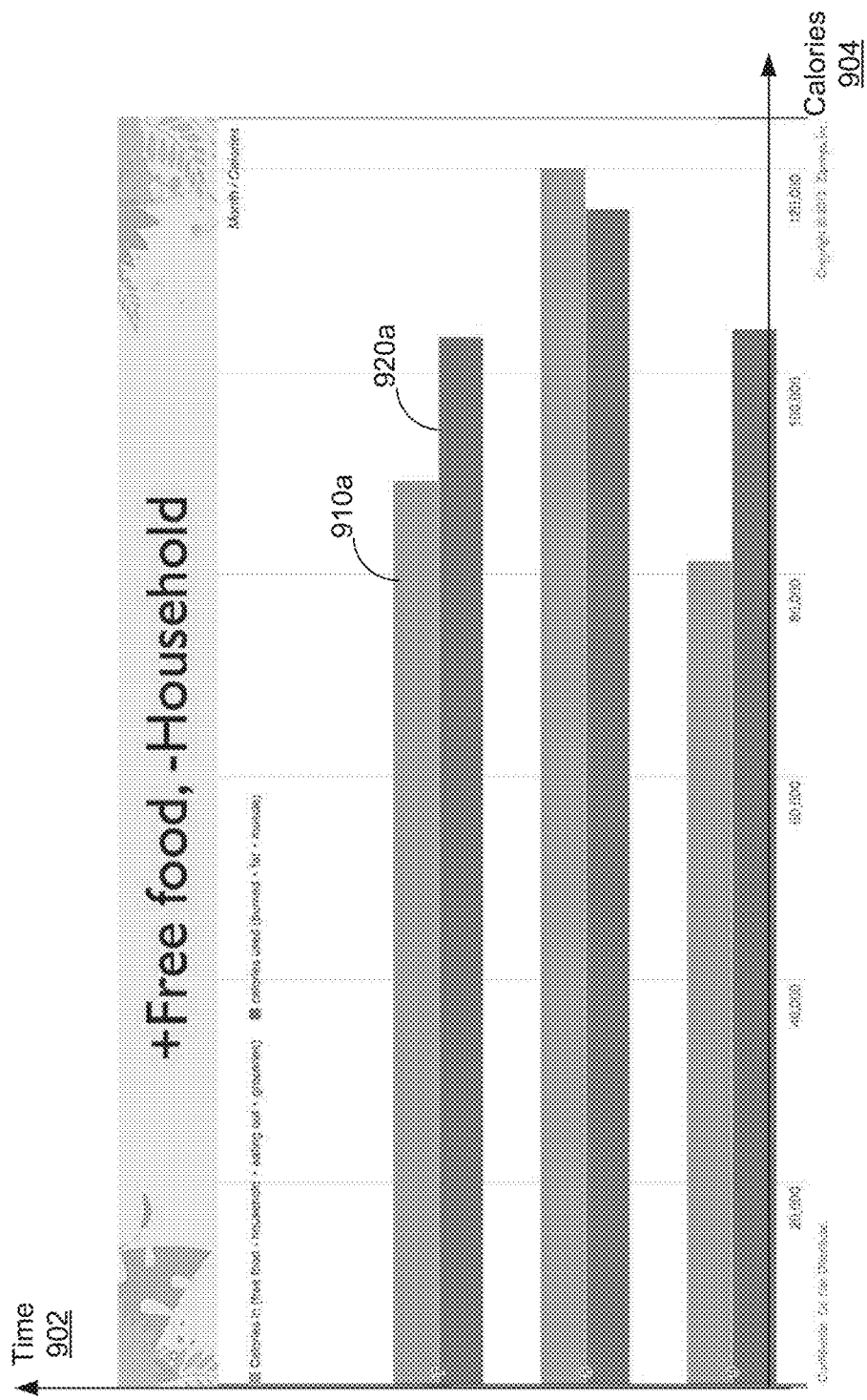
FIG. 9 shows examples of further increased accuracy of nutrition tracking based on user grocery purchase data, restaurant purchase data and other contributors to user calories/nutrient consumption.

Passively tracking food consumption of a user by considering a variety of food consumption sources, such as grocery loyalty shopping card data, scanning receipts from vendors that do not use linked loyalty rewards cards, restaurant credit card and point of sale purchase data, estimates of food consumption within a household, estimates of free food intake and estimates of food pantry use, increases accuracy of food consumption. Comparing with the food consumption data illustrated in FIG. 7, FIG. 8 and FIG. 9 show examples of increased accuracy of nutrition tracking of the same user over the same tracking period. For example, FIG. 8 shows examples of increased accuracy of nutrition tracking based on both user grocery purchase data and restaurant purchase data, powered by the passive tracking service. The discrepancy between the calories based on tracked food consumption from the user's grocery purchase data and restaurant purchase data for the first month, 810a, and the calories based on the energy expenditure for the first month, 820a, is smaller than the corresponding discrepancy in FIG. 7. The similar trend is observed for the other two months, e.g., 810b vs. 820b and 810c vs. 820c.

FIG. 9 shows examples of further increased accuracy of nutrition tracking by the passive tracking service based on user grocery purchase data, restaurant purchase data and other contributors to user calories and nutrients consumption in terms of the further reduced discrepancy between the calories from the tracked food consumption, 910a, and the calories from the user's energy expenditure, 920a. Experimental data shows (e.g., FIG. 10) that food consumption based on grocery purchase data, restaurant dining data, free food, pantry usage and shared food accounts for 95% of all calories actually consumed by users; the rest can be estimated based on population norms by the passive tracking service.

Referring back to FIG. 3, it is noted that not every food purchase venue issues purchase loyalty reward cards or uses a point of sales system that specifically tracks individual food items for its customers and, is directly connected to the passive nutrition tracking service 130. However, the development of new technologies, especially wireless based technologies, has enabled the passive nutrition tracking provided by the passive nutrition tracking service 130 in the absence of purchase loyalty reward cards and/or a point of sale system. One such enablement is based on the use of radio-frequency identification (RFID) on food containers or plates, tied to indoor local positioning systems based on RFID base station and Bluetooth technology, linked to user mobile phones, and further connected to the passive nutrition tracking using other embodiments of the calorie tracking module 210.

Figure 16:
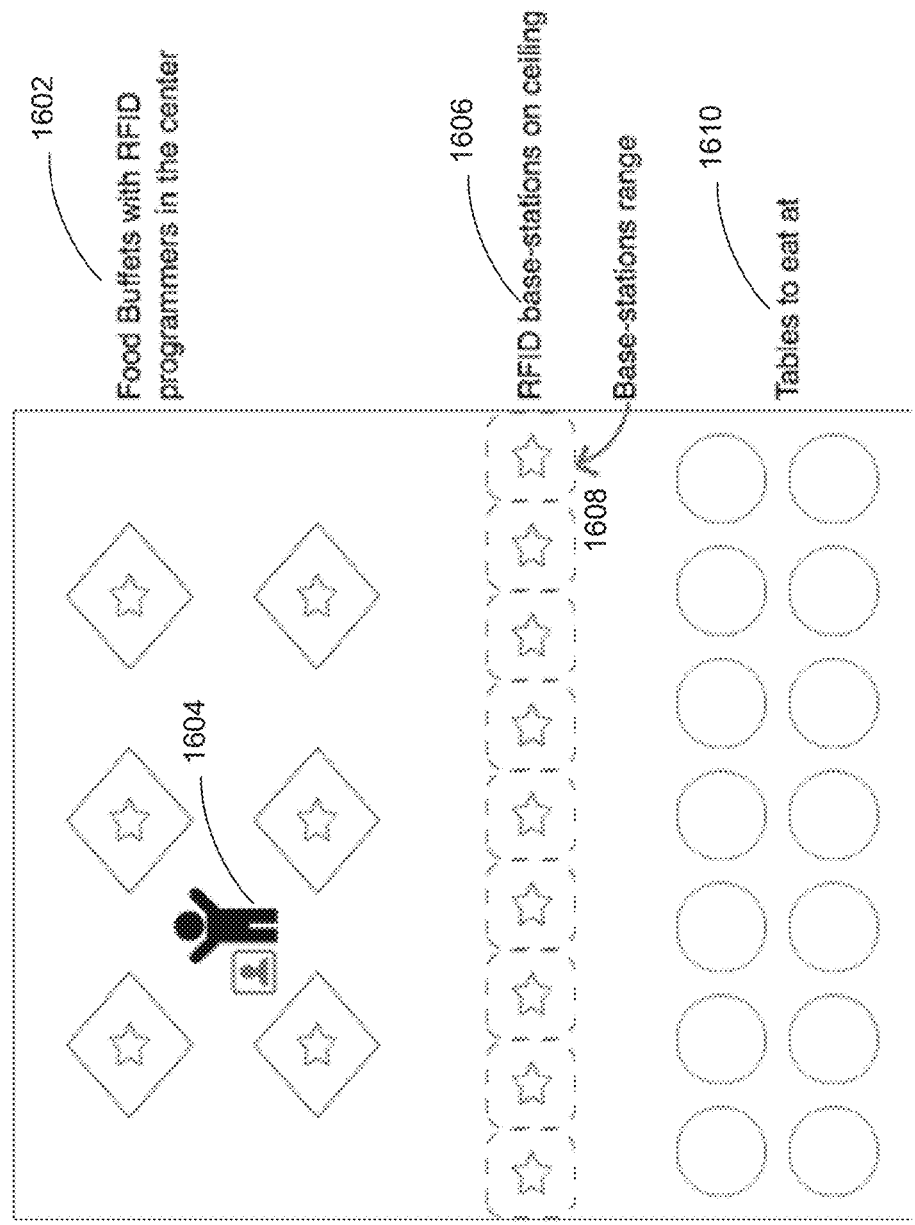
FIG. 16 shows an example of radio-frequency identification (RFID) based passive tracking of food selected by a user in a cafeteria.
Figure 17:
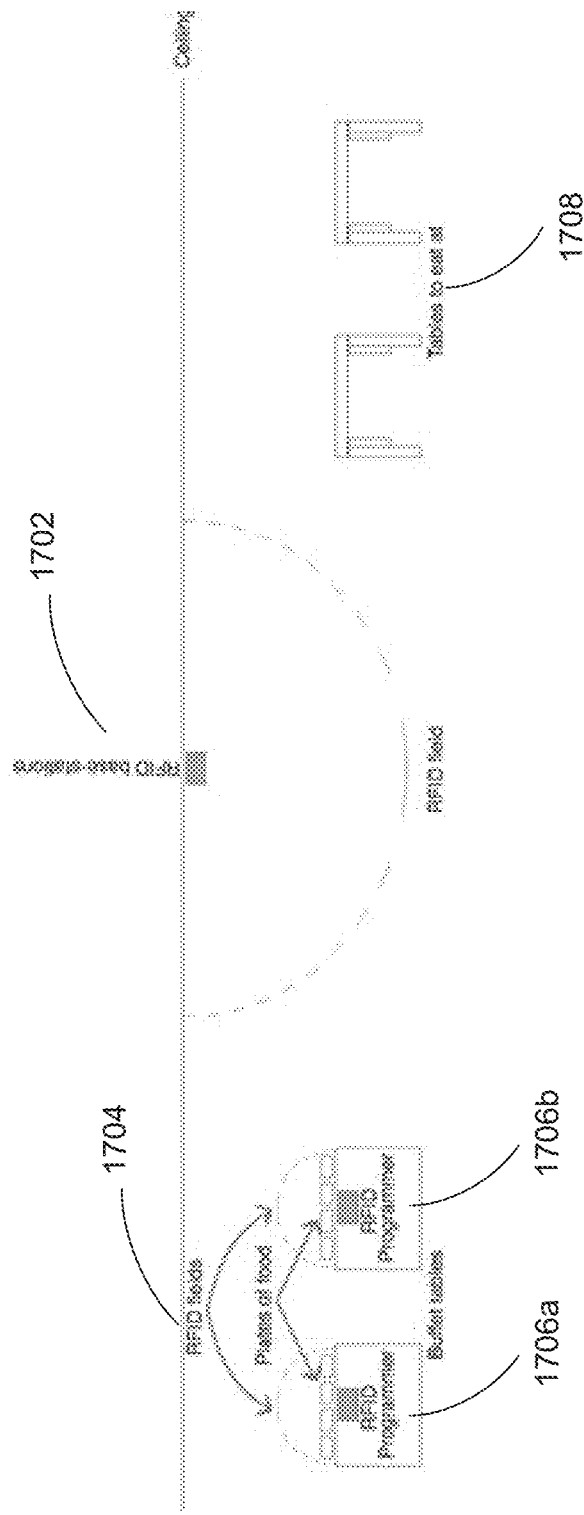
FIG. 17 shows a different view of the RFID based passive food tracking illustrated in FIG. 16.

FIG. 16 shows an example of RFID based passive tracking of food selected by a user in a cafeteria. In the example shown in FIG. 16, RFID encoders are mounted under the middle of the cafeteria buffet tables 1610 (or under trays, upon which the dining plates are placed). The dining plates and their attached RFID tags are programmed with the dish information after sitting on the RFID encoders (on buffet tables or trays) for more than 5 seconds. RFID bases stations are amounted along the ceiling 1606 between the buffets 1602 and the dining tables 1610. Each RFID base station has a receiving range (e.g., the dotted circle of the right most RFID base station 1608). Diners in the cafeteria are carrying the RFID-based identification (ID) cards, e.g., employment ID cards. When a diner crosses the line of RFID base stations in the ceiling, the RFID base stations read the dinner's ID card and the RFID tags in each of the diner's plates. The dish information and the diner's ID from the RFID base station is logged by the calorie tracking module 210 (along with the date and time) into the user food history database 134 of the passive nutrition tracking service 130. FIG. 17 shows a different view of the RFID based passive food tracking illustrated in FIG. 16.

Figure 18:
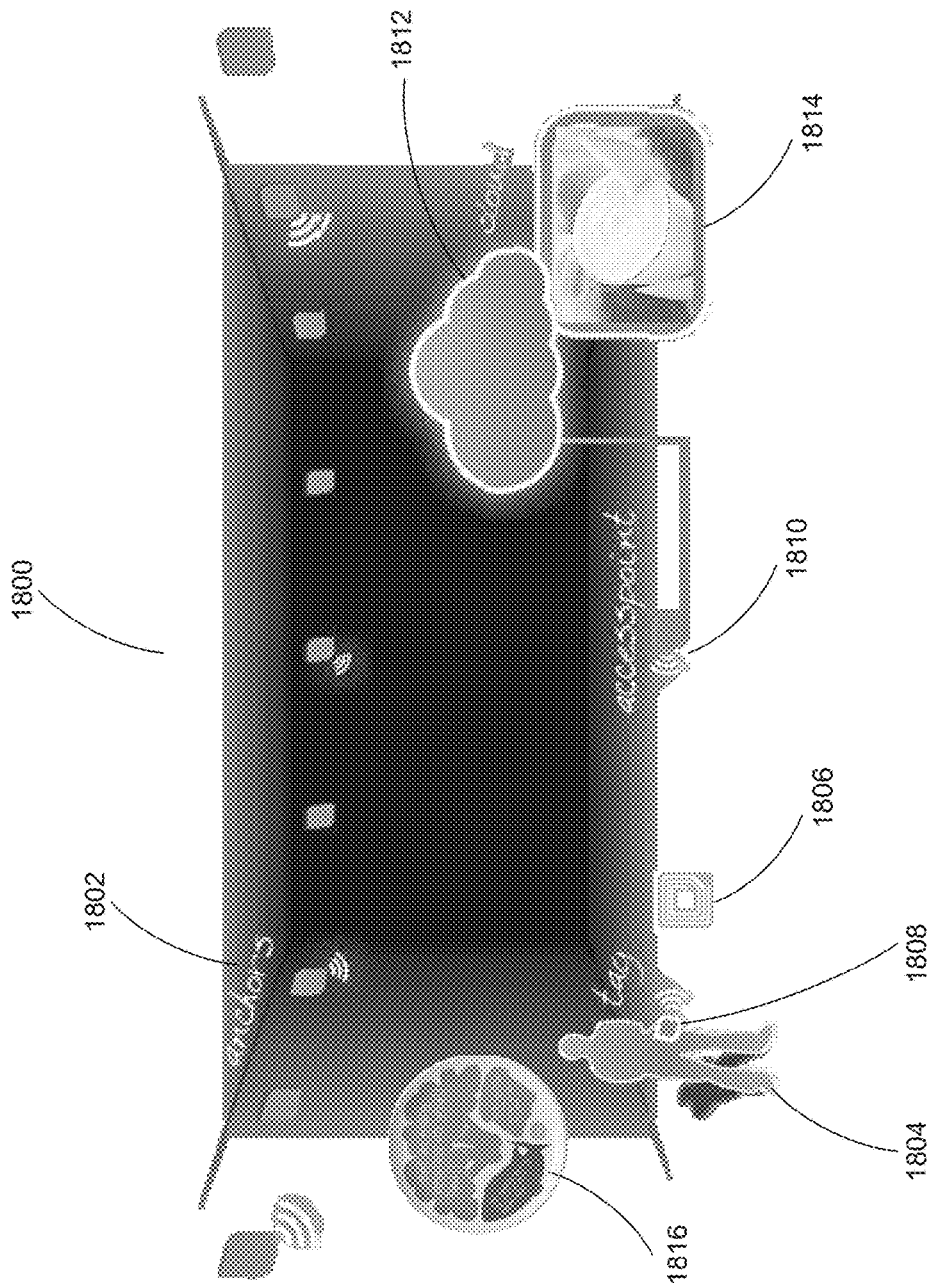
FIG. 18 shows another example of passive food tracking based on a combination of RRID and Bluetooth wireless technology.

FIG. 18 shows another example of passive food tracking 1800 based on a combination of RFID and Bluetooth wireless technology. In the example shown in FIG. 18, the line of RFID bases stations 1802 mounted along the ceiling also contain Bluetooth transceivers, which recognize a user 1804 based the Bluetooth MAC address of the user's smart phone 1808. The food consumption data received from the RFID enabled dining plate 1806 associated with the user ID is transmitted over a cloud network 1812 via an access point 1810 to the calorie tracking module 210. In summary, the Bluetooth beacons locate the users mobile phone, which in turn identifies the user, and which triggers it to send information about the RFID tag on the plate next to the user for over a fixed period of time; this RFID tag is encoded with an identifier that links it to the appropriate food placed on that plate, that day. The calorie tracking module 210 stores the received data in the user food history database 134 of the passive nutrition tracking service 130 for further processing, such as estimating calories and nutrient levels contained in the tracked food 1814 and recommending healthy lifestyle tips 1816 based on the estimation.

The passive food tracking 1800 illustrated in FIG. 18 can be modified as a Bluetooth only system. In this scenario, all RFID tags are replaced with Bluetooth transmitters (also referred to as "beacons"), and the line of RFID bases stations are replaced with Bluetooth transceivers. The Bluetooth transceivers are configured to recognize a user from their smart phone's Bluetooth MAC address and detect dining plates that are embedded in or attached to the Bluetooth beacons.

In a scenario where a purchase venue requires manual checkout with purchases, a point of sale system can be integrated into the passive nutrition tracking service 130, instead of tracking the food consumption through sensors, e.g., the RFID tags attached to the dining plates in FIG. 16 and FIG. 18. For example, the point of sale system can be provided with the items manually entered by a human clerk, by scanning barcodes and Quick Response (QR) codes of purchased items. After the check out, the purchased items and the identity of the purchaser are transmitted from the point of sale system to the passive nutrition tracking service 130 for further processing.

Referring back to FIG. 2, the tracking engine 200 maps the passively tracked food consumption data against the information stored in the food terminology index and nutrition database 132 through the mapping module 220. In one embodiment, the mapping module 220 identifies the type of food in the food consumption data using a variety of identification methods, such as text recognition (e.g., optical character recognition) of a scanned purchase receipt, image recognition for food items in a captured restaurant dish, or voice recognition of audio entries of a food journal. Other identification techniques known to those of ordinary skill in the art, e.g., GPS tagging and barcode image interpretation, are readily available for use by the mapping module 220.

Upon the identification of each food item in the food consumption data, the mapping module 220 retrieves one or more food tables and associated nutrients tables related to each identified food item. The mapping module 220 sends the retrieved food tables and associated nutrients tables along with the identification and type of the food item to other modules of the tracking engine 200 for further processing.

The energy expenditure module 230 of the tracking engine 200 tracks user energy expenditure data measured by one or more energy factors, including user physical activity, changes in weigh, muscle and fat gain, food waste and spoilage. In one embodiment, the energy expenditure module 230 receives user physical activity data from a wearable electronic device worn by a user. The wearable electronic device has a built-in accelerometer and is worn by a user on his/her wrist, arm, waist, in clothing or shoes to measure his/her movement. The energy expenditure module 230 receives user weigh change data from a wireless-based scale that sends weight and body fat percentage information of the user over the Internet. The energy expenditure module 230 may receive other types of user data, such as number of hours of sleep, user's mood and stress level, which modulates metabolism (e.g., very happy, very sad).

The estimation module 240 estimates the calories and nutrients levels of a user based on the food consumption data and associated food tables and nutrient tables. In one embodiment, the estimation module 240 generates the total calories of the food consumption based on calories associated with each identified individual food item contained in the food consumption data. The estimation module 240 also generates a list of identified nutrients and nutrients levels, based on population level norms from NHANES data from the CDC and Institute of Medicine recommended values. For example, the estimation module 240 estimates the user energy intake (EI) using population data from doubly-labeled water studies, and fatty acids and folate acids studies, conducted as part of the NHANES studies.

The correlation module 250 corrects the estimated calories and nutrients levels associated with the food consumption in relation to user energy expenditure data. In one embodiment, the correlation module 250 corrects the estimated calories and nutrients levels using one or more correction algorithms that account for user energy expenditure based on the health statistics in the CDC NHANES repository. For example, the correlation module 250 modifies the estimated calories and nutrients levels by considering the effects of the passively tracked user physical activity, changes in user weight, food waste, food sharing, food spoilage and food storage usage. The corrected estimated calories and nutrients accurately reflects the amount of calories consumption and its associated nutrients levels and detects significant changes in diet and nutrients levels over a period of time. For example, for a particular nutrient, the correlation module 250 generates a predicted average daily intake of that nutrient for a user based on the passive tracking of the user's food consumption.

The correlation module 240 further corrects the estimated calories and nutrients levels for a user based on the user's demographic and genetic information, such as race, gender, age and mutations which may affect metabolism of certain nutrients. In one embodiment, the correlation module 240 compares the estimated nutrients levels for a user with corresponding normalized society nutrients levels, where the user shares the same or similar demographic and genetic characteristics with the ones of the corresponding normalized society population. Considering a user's demographic and genetic characteristics in calories and nutrients levels estimation further enhances the accuracy of the user's dietary history.

The generation module 260 generates user dietary history and one or more personalized healthy lifestyle recommendations to the user based on the analysis of the passively tracked food consumption and energy expenditure. The passive tracking service extrapolates the proportion of nutrients purchased—normalized to an average over a period of time—to a level that matches the caloric intake of the user; percentage of daily recommended daily intake is further shown based on Institute of Medicine published recommended daily intake levels for different nutrients, for different types of people. In one embodiment, the generation module 260 generates user dietary history, which is publishable online over the Internet. The generated user dietary history can be presented in a variety of ways, which are easy for user to digest and to share with others. For example, the user dietary history includes calories consumed and nutrients levels for the user over a period of time, e.g., a day, week, month or year. The user dietary history can also include trends of user's calories/nutrients consumption over a specified period of time.

The generation module 260 also generates one or more personalized healthy lifestyle recommendations to the user based on the analysis of the passively tracked food consumption and energy expenditure. For example, the generation module 260 may recommend one or more recipes based on the user's recent purchase of a food item. In response to amount of carbohydrates intake lower than a threshold value, the generation module 260 may recommend add whole wheat into the user's daily diet. The generation module 260 can also generate health warnings in response to unhealthy increase of any given nutrient, especially in relationship known disease outcomes and risk factors that nutrient is correlated with, for example, an increase in saturated fat intake detected in the user's diet history, simultaneous with an increase in the users LDL cholesterol blood levels.

The interface module 270 interacts with the client device 110 and other modules of the tracking engine 200 to present user dietary history and personalized healthy lifestyle recommendations in a user friendly way. In one embodiment, the interface module 270 creates an interactive graphic user interface to present user dietary history, where users can interactively navigate the content of the dietary history.

Figure 4:
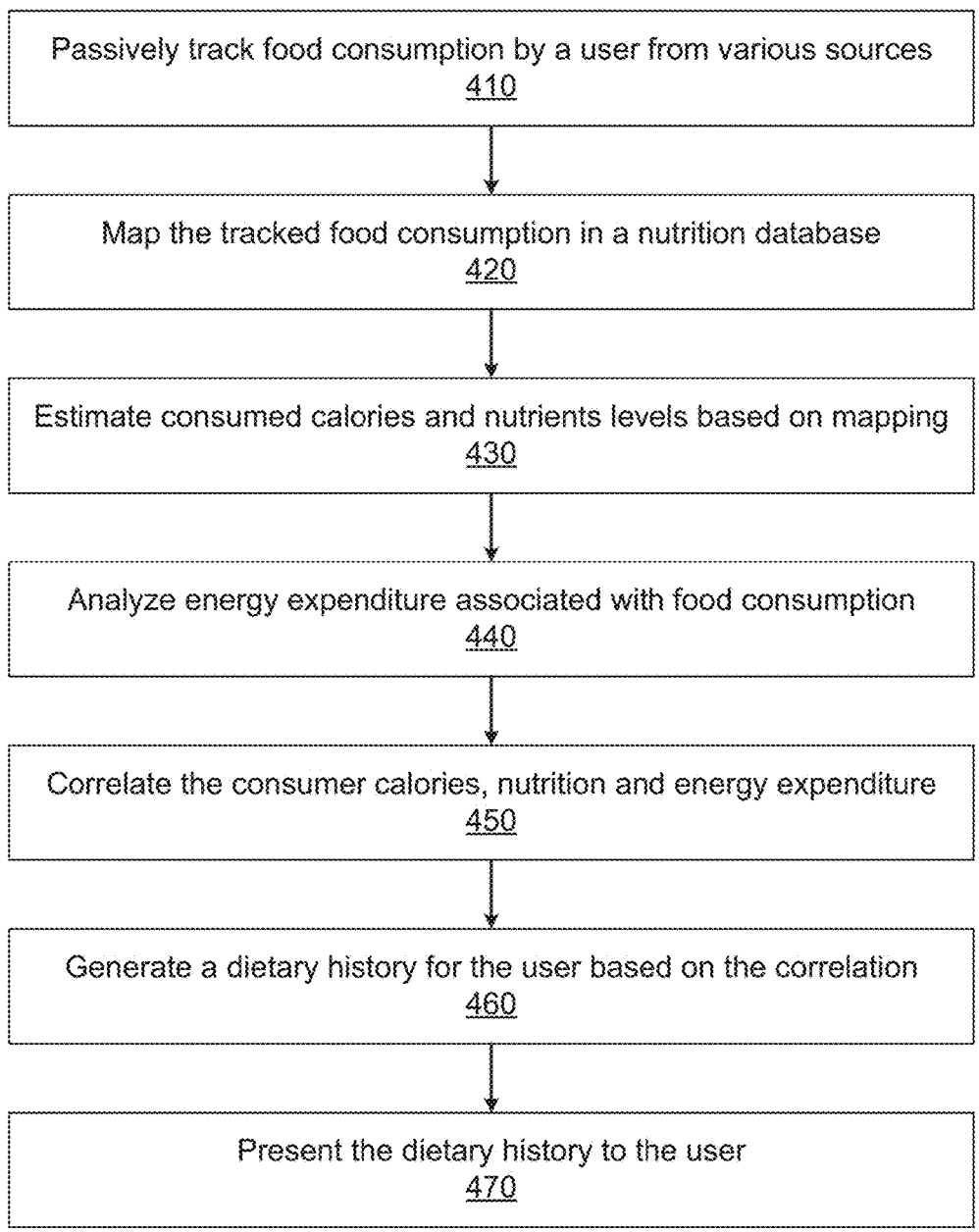
FIG. 4 is an exemplary flowchart illustrating a process of passive nutrition tracking according to one embodiment.

FIG. 4 is an exemplary flowchart illustrating a process of passive nutrition tracking according to one embodiment. Initially, the passive nutrition tracking service 130 passively tracks 410 food consumption by a user from various sources, e.g., food purchases from grocery shopping and dining in restaurants, free food and the usage of the user's household food pantry. The service 130 maps 420 the tracked food consumption in a nutrition database, e.g., the food terminology index and nutrition database 132. The service 130 estimates 430 consumed calories and nutrients levels based on the mapping. The service 130 tracks and analyzes 440 user energy expenditure associated with the passively tracked food consumption, where the user energy expenditure is measured by user physical activity, muscle and fat gain and waste output of the user. The service 130 correlates 450 the estimated calories and nutrients levels with the user energy expenditure by correcting the estimated calories and nutrients based on the user energy expenditure data. The service 130 generates 460 a dietary history for the user based on the correlation and presents 470 the dietary history to the user in a user friendly way. Additionally, the service 130 generates one or more personalized healthy lifestyle recommendations based on the passively tracked food consumption of the user.

Presentation of Dietary History and Recommendations

Figure 11:
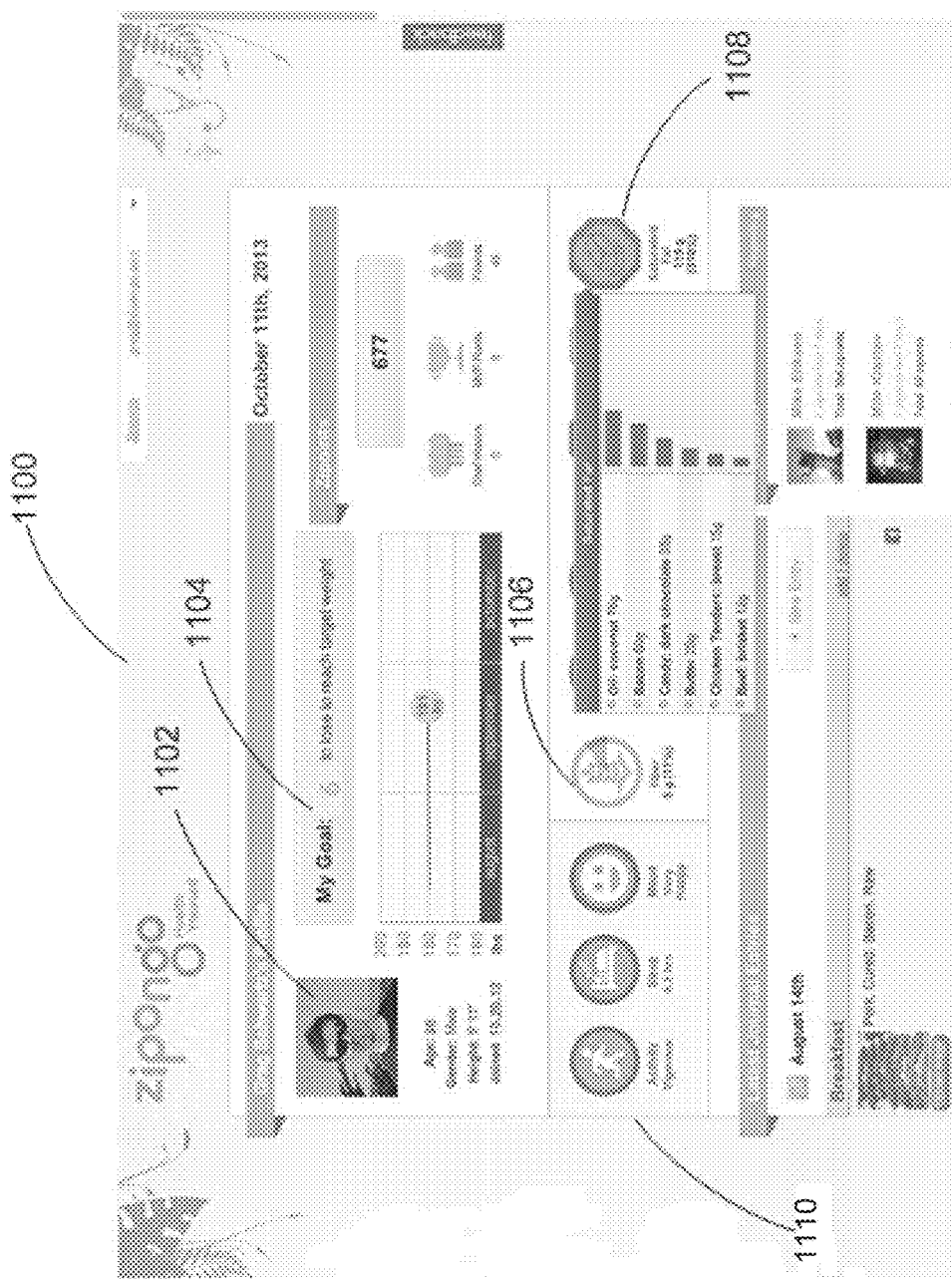
FIG. 11 shows a graphical user interface for users to interact with their customized dietary history.

FIG. 11 shows a graphical user interface (GUI) 1100 for users to interact with their customized dietary history. The GUI displays user information 1102 retrieved from the user profile stored in the user food history database 134 of the pass nutrition tracking service 130. The user information may include a user profile picture, age, gender, and height and membership information. The dietary history may include graphical presentation of user's energy expenditure 1110 in terms of level of physical activity (e.g., vigorous), number of hours of sleep (e.g., 6.5 hours) and mood (e.g., very happy). The dietary history also includes key nutrients information, such as fiber 1106 and saturated fat 1108. User can interact with his/her dietary history, such as clicking the saturated fat symbol 1108, which displays a drop down window listing various types of food that contributed to the saturated fat intake and amount of contribution from each type of good. The GUI also includes a health management planner 1104, which motivates the user and allows the user to set up health goals based on his/her dietary history.

Figure 12:
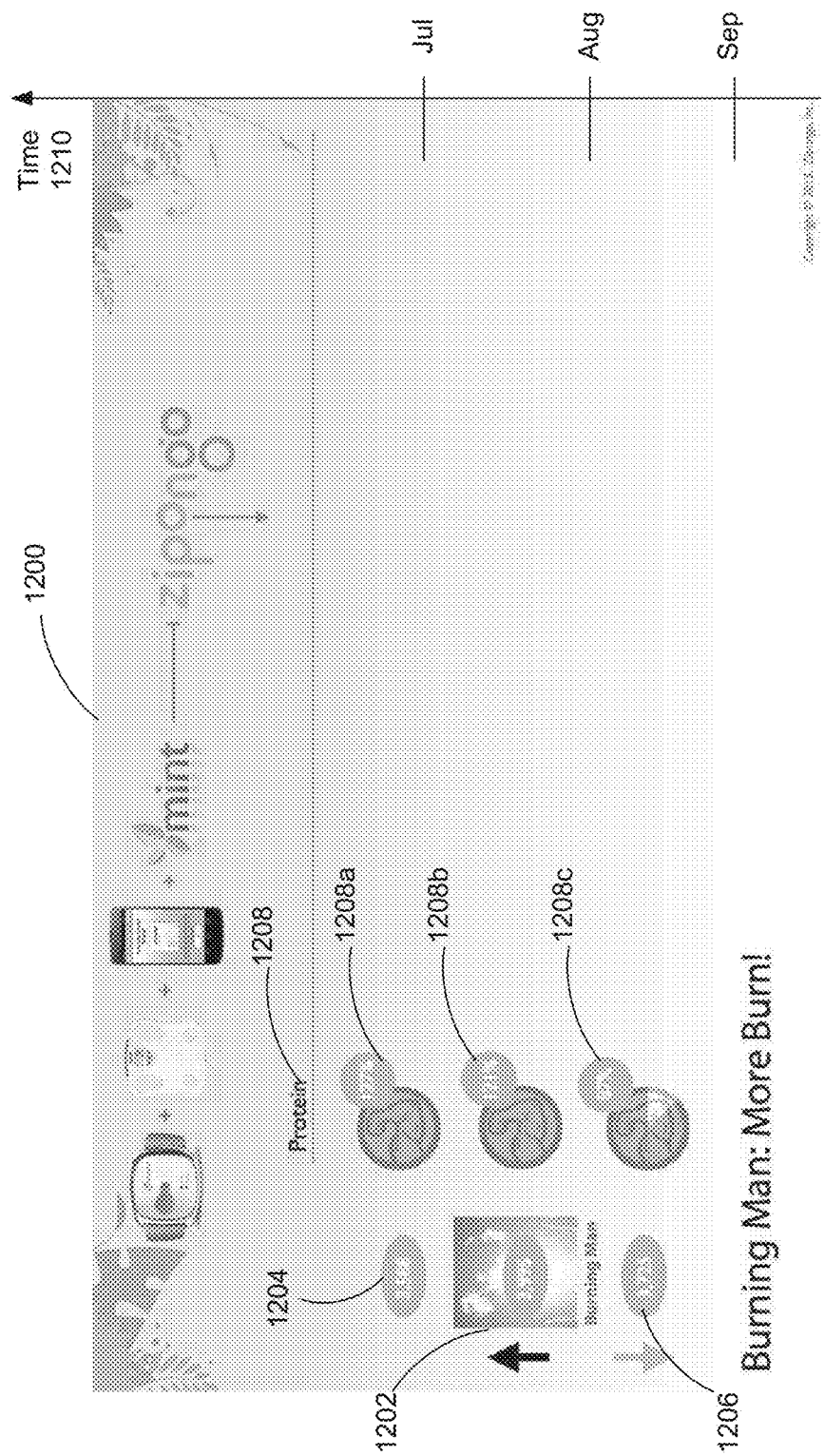
FIG. 12 illustrates an exemplary graphical user interface for presenting a user's levels of protein intake predicted based on passive nutrition tracking associated with the user.

FIG. 12 illustrates an exemplary GUI 1200 for presenting a user's levels of protein intake predicted based on passive nutrition tracking associated with the user. The example in FIG. 12 shows average daily intake of calories and protein over three months period (July, August and September) based on the passively tracked user food consumption as described above. The predicted average daily intake of calories for the user is 3,588 calories for July (1204), 3,995 calories for August (1202), and 3,725 calories for September (1206). For the nutrient protein 1208, the dietary history shown in FIG. 12 shows the percentage of the predicted average daily intake of protein based on the passive nutrition tracking over the recommended daily allowance for protein based on society data, e.g., the NHANES statistics. For example, the percent for protein intake for July is 127% (1208a), 121% for August (1208b) and 87% for September (1208c). Comparing the protein intakes over the monitored three months, the dietary history of the user shows a big drop in protein intake in September. Upon the detection of such change, the passive nutrition tracking service 130 may generate a personalized recommendation to the user for increasing his/her daily protein intake. Further, the cholesterol and saturated fat for the user was very high over this time period, and their LDL cholesterol blood levels also increased, so they might receive a recommendation to reduce cholesterol and saturated fat intake—with specific food changes recommended (such as less bacon and less coconut oil).

Figure 13:
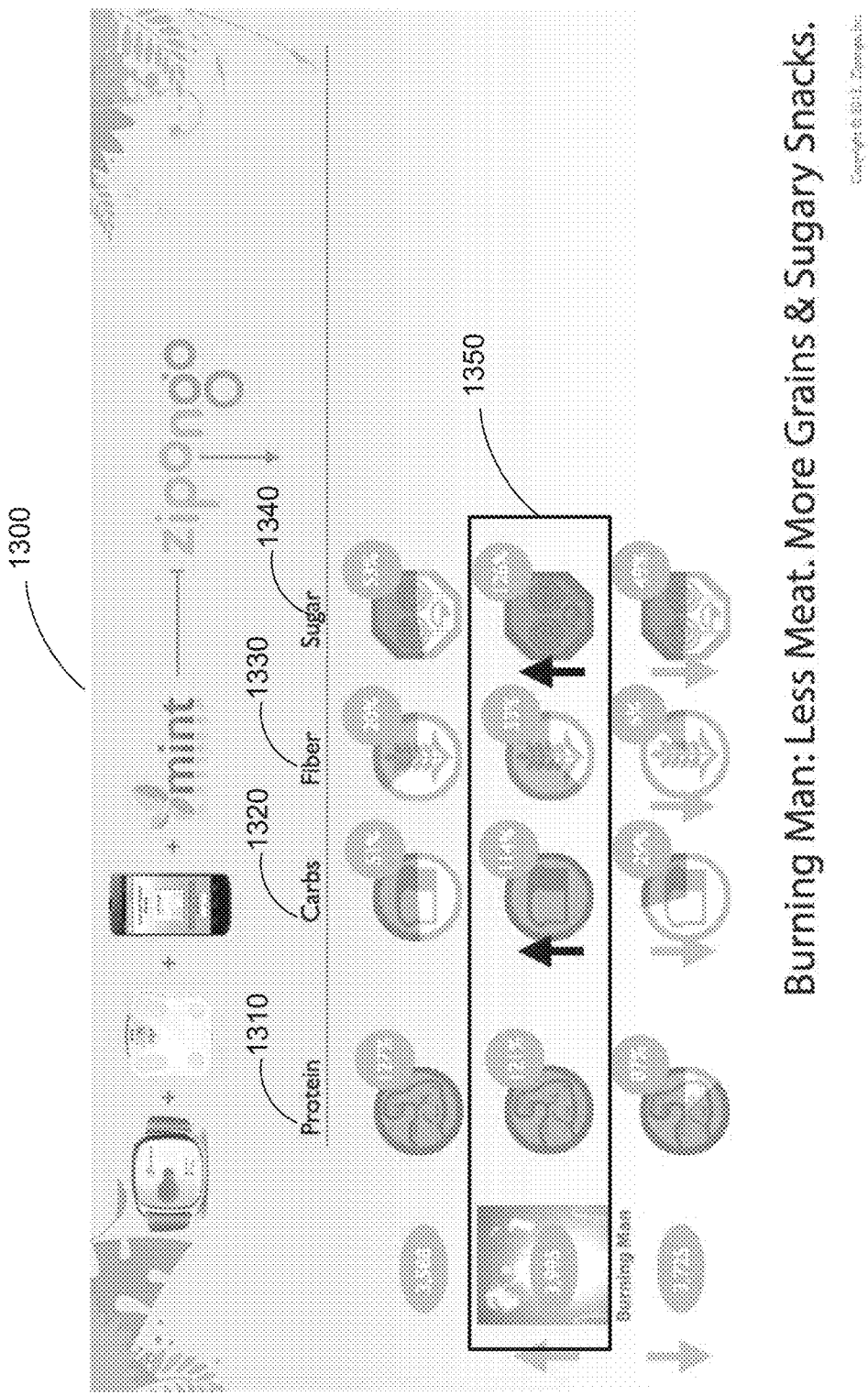
FIG. 13 illustrates an exemplary graphical user interface for presenting a user's levels of various nutrients intake predicted based on passive nutrition tracking associated with the user.

FIG. 13 illustrates an exemplary GUI 1300 for presenting a user's levels of various nutrients intake predicted based on passive nutrition tracking associated with the user. The dietary history shown in FIG. 13 includes predicted average daily intake of nutrients of protein 1310, carbs 1320, fiber 1330 and sugar 1340. The monthly data for the user, e.g., 1350 for August, shows that the user was likely to have consumed more grains and sugary snacks for that month.

Figure 14:
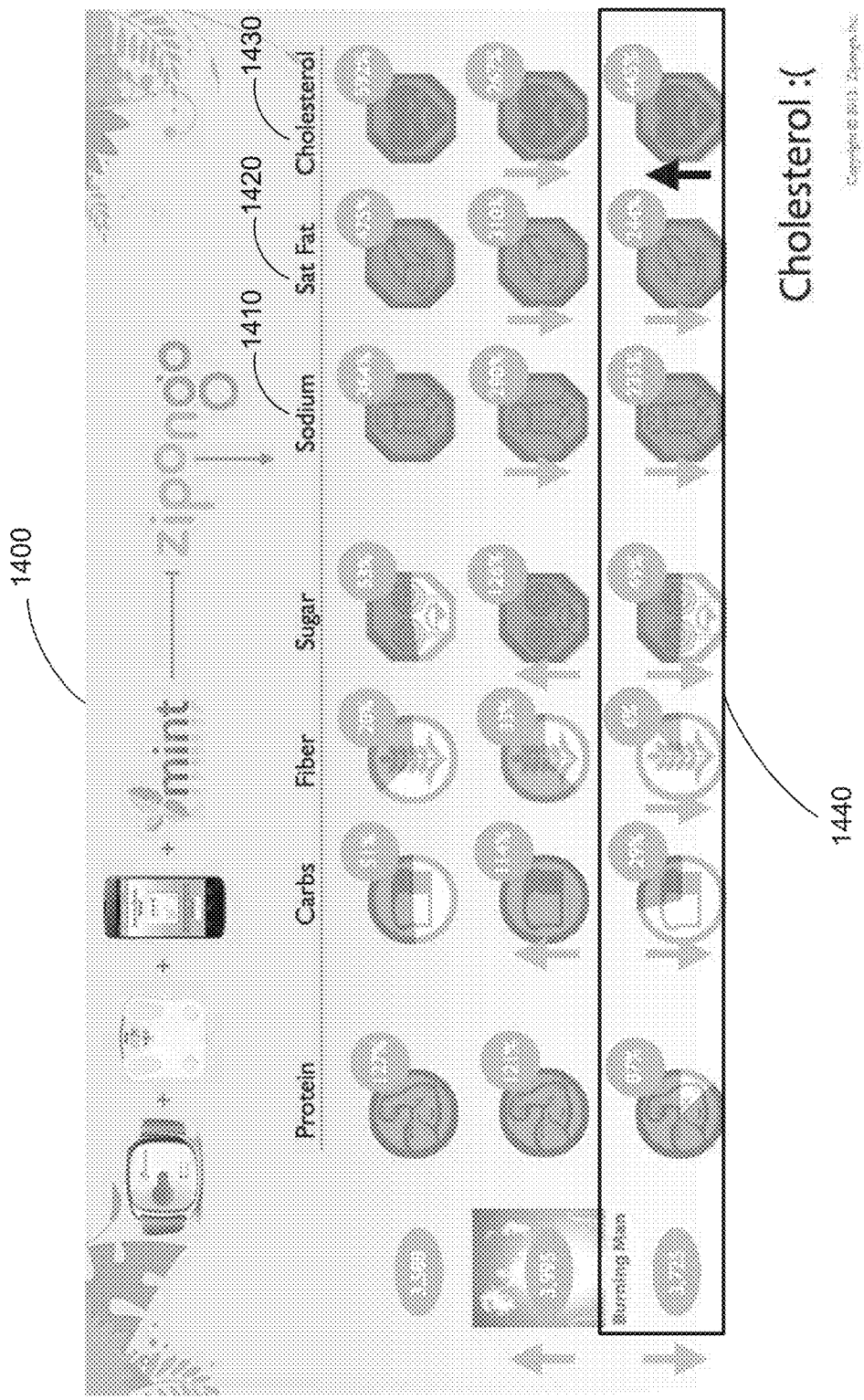
FIG. 14 illustrates another example of graphical user interface for presenting a user's levels of various nutrients intake predicted based passive nutrition tracking associated with the user.
Figure 15:
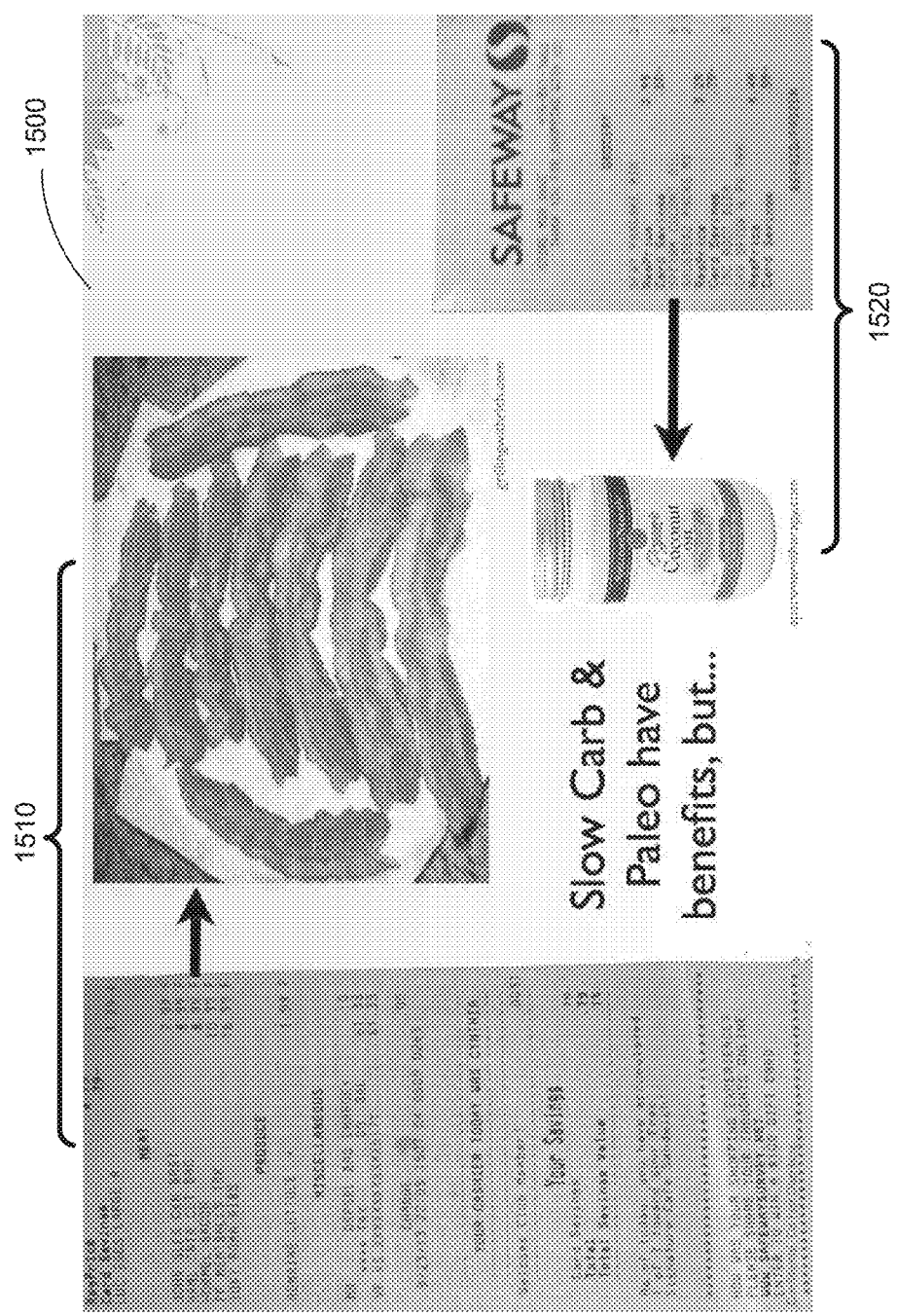
FIG. 15 illustrates an example of display of food items that contribute to changes of a user's nutrients intake.

FIG. 14 illustrates another example of GUI 1400 for presenting a user's levels of various nutrients intake predicted based passive nutrition tracking associated with the user. The dietary history shown in FIG. 14 includes predicted average daily intake of sodium 1410, saturated fat 1420 and cholesterol intake 1430 in addition to nutrients of protein, carbs, fiber and sugar. The monthly data for the user, e.g., 1440 for September, shows that the user was very likely to have consumed very high sodium, saturated fat and cholesterol intake. The food purchase history of the user corresponding to the same tracking period shows that the user had stopped buying cheese and started buying bacon as a substitute for cheese. The food purchase history of the user corresponding to the same tracking period further shows that the user started buying coconut oil instead of olive oil. FIG. 15 illustrates an example 1500 of display of food items that contribute to the changes of a user's nutrients intake, e.g., bacon 1510 and coconut oil 1520. By linking the user's food purchases with his dietary history, the passive nutrition tracking service 130 is able to specifically pinpoint the high likelihood of the user's nutritional problems and to provide personalized health living tips.

Application of Passive Nutrition Tracking

The solution for passively and automatically tracking user food consumption described above can be beneficial to the entire population in proving health behavior change programs. With a large percentage of a population having access to long-term consistent information on their diet and receiving true estimates of change in nutrients over time, people can better respond to healthy lifestyle recommendations. Further, the quality of personalized recommendations for how to modify one's diet can also be improved. Reducing or eliminating the burden of lifestyle tracking has great potential to expend the reach and effectiveness of self-monitoring programs.

Figure 19:
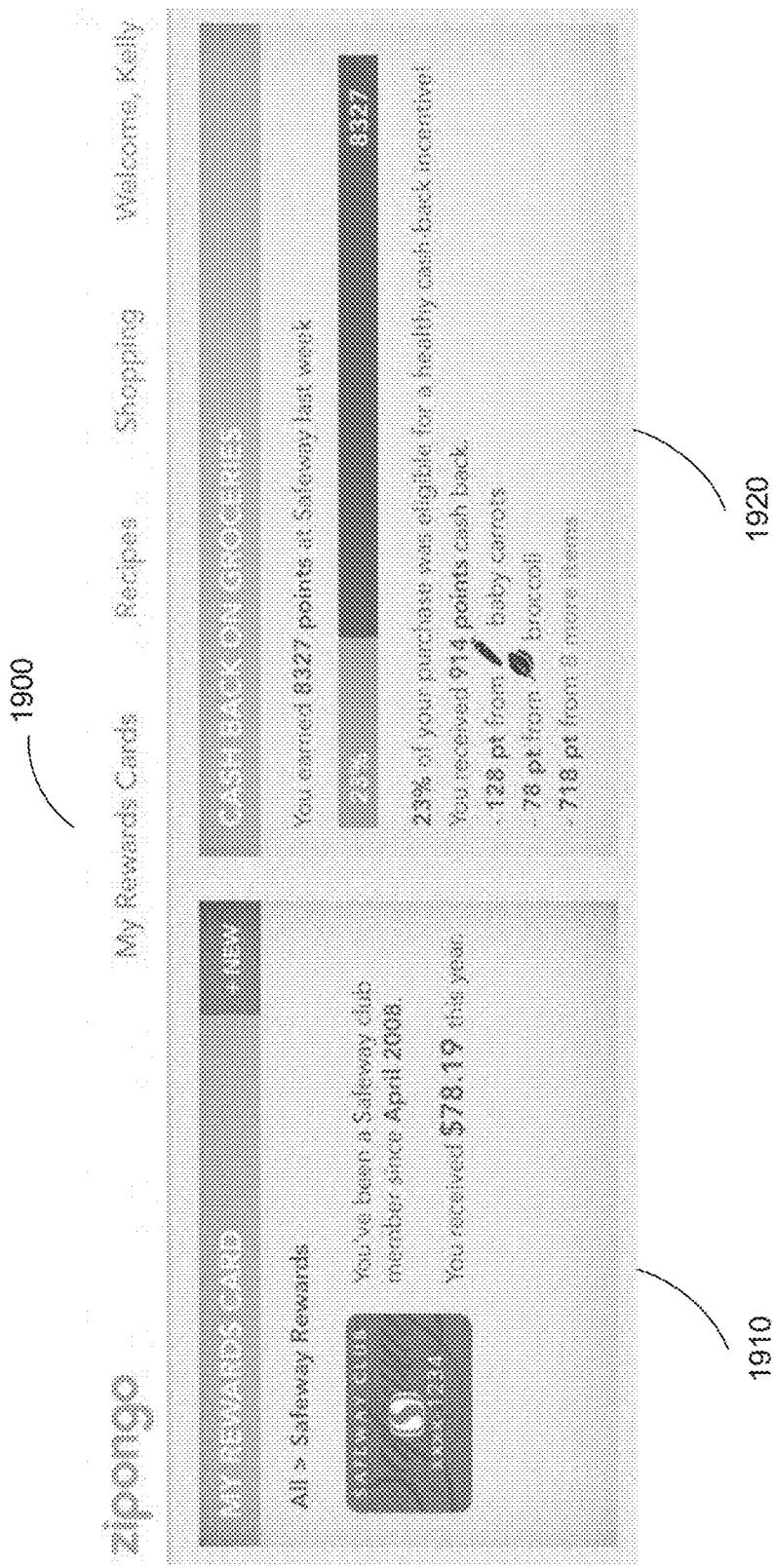
FIG. 19 shows an example of a user login webpage of passive nutrition tracking service illustrated in FIG. 1.

The following figures illustrate an application of the solution to passive nutrition tracking of a user named Kelly. In this example, user Kelly has a SAFEWAY™ reward card, which was registered once with the passive nutrition tracking service 130. FIG. 19 shows an example of Kelly's login webpage 1900 of the passive nutrition tracking service illustrated in FIG. 1. Kelly's SAFEWAY™ reward card 1910 is shown on the left side, which indicates that Kelly has been a member since April 2008 and has received a cash reward, $78, 19, for this current year. The right side 1920 displays the details of the cash back rewards for Kelly for the past week, including percentage of points eligible for a healthy cash-bask incentive.

Figure 20:
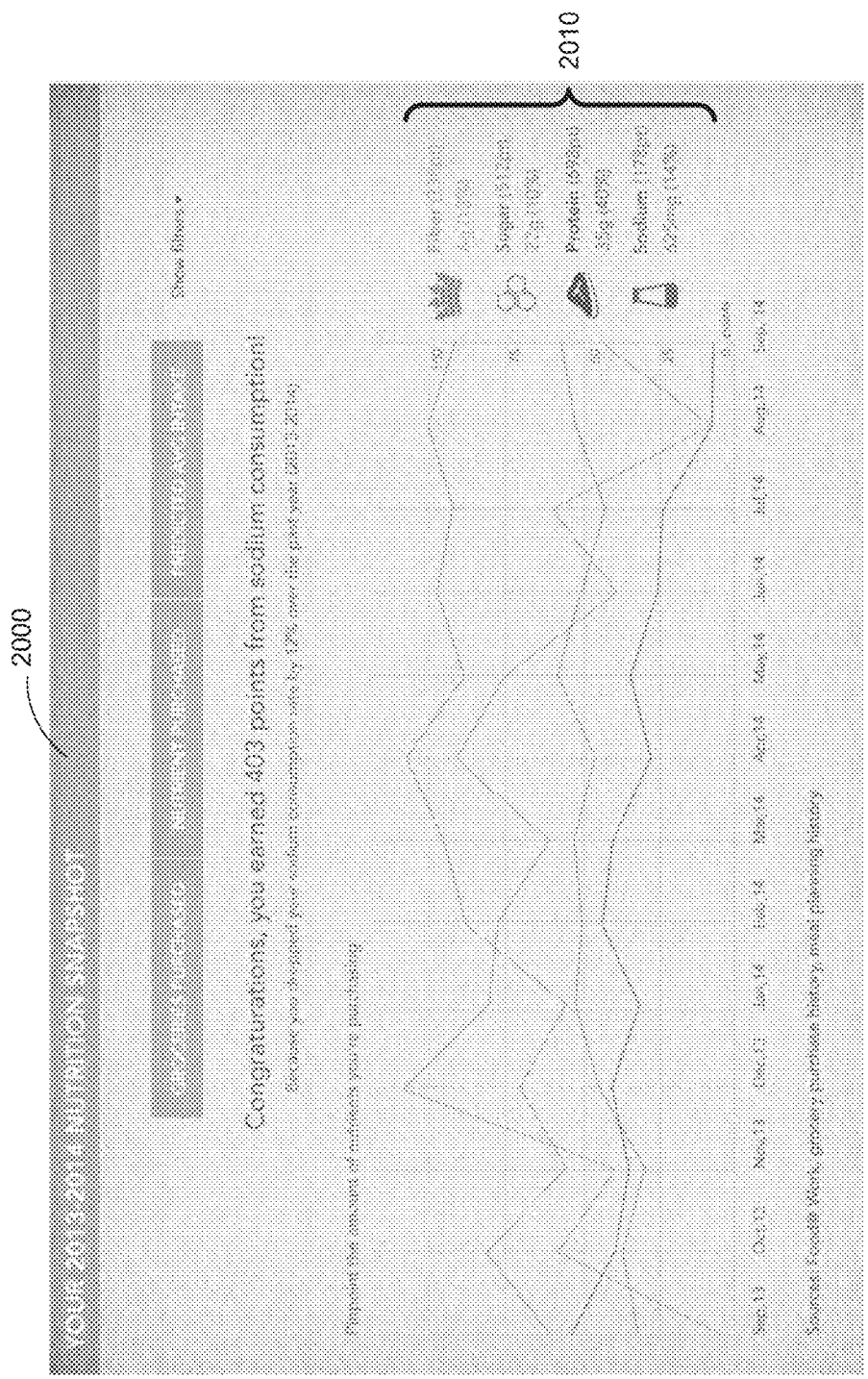
FIG. 20 shows a yearly trend of nutrition intake of a user based on passive nutrition tracking.

FIG. 20 shows a yearly trend of nutrition intake of Kelly over year 2013 and year 2014 based on passive nutrition tracking of Kelly's SAFEWAY™ grocery purchases. The trend 2010 shows the changes of amount of nutrients of fiber, sugar, protein and sodium based on Kelly's grocery purchases over one year. The graphical presentation of the trend is easy for Kelly to understand her dietary history and nutritional balance among various nutrients.

Figure 21:
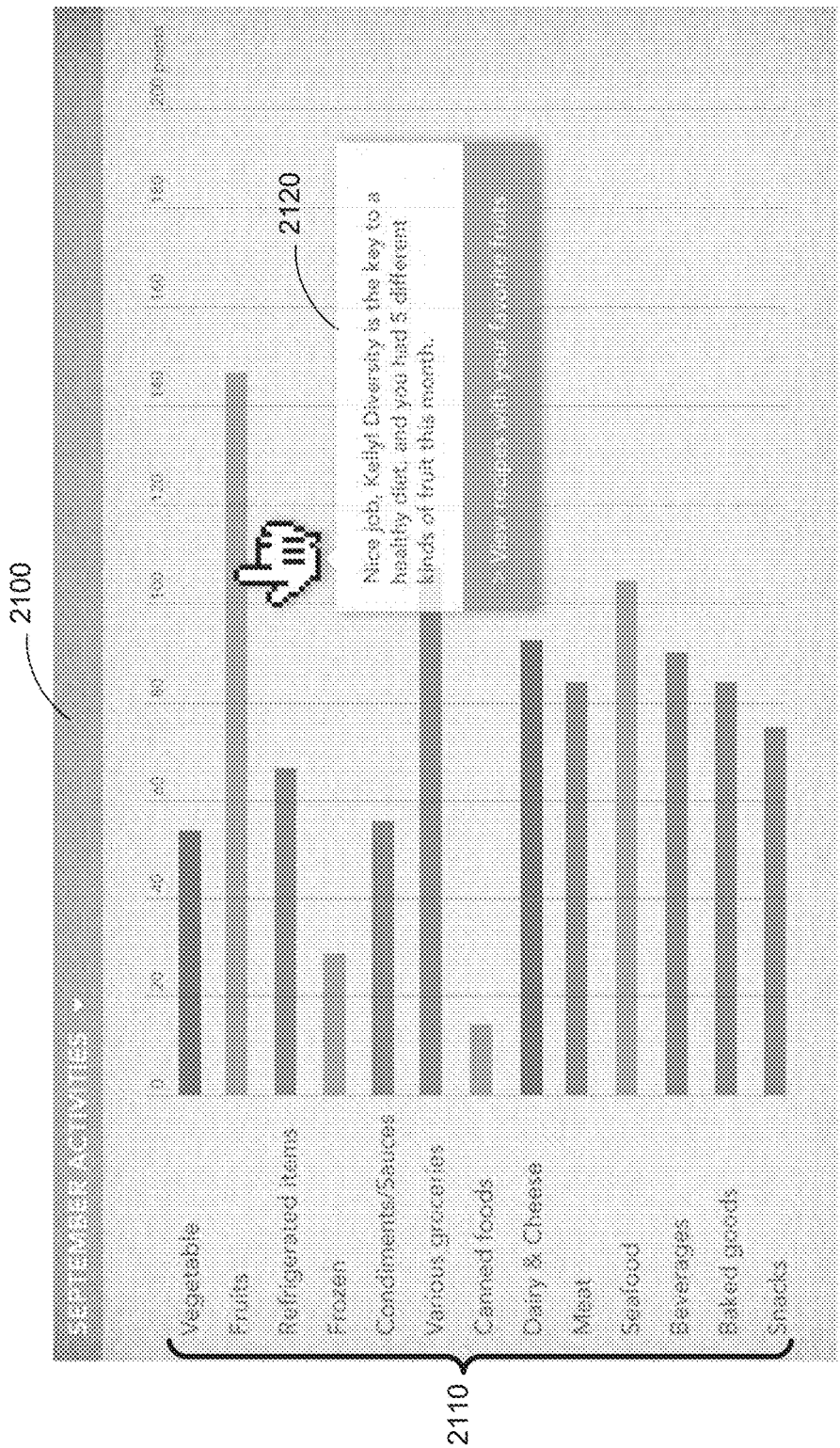
FIG. 21 shows a monthly trend of nutrition intake of a user based on passive nutrition tracking.

FIG. 21 shows a monthly trend of nutrition intake of Kelly for September based on passive nutrition tracking Kelly's SAFEWAY™ grocery purchases. The dietary history of September for Kelly shows various types of food 2110 she has purchased in that month, e.g., vegetable, fruits, refrigerated items, frozen food, sauces, canned foods, dairy and cheese, meet, seafood, beverages, baked goods and snacks. The dietary history also shows amount of purchase from each type of food measured in SAFEWAY™ reward points. The dietary history also includes incentive tips to encourage healthy lifestyle demonstrated by Kelly. For example, Kelly received a nice comment 2120 from the passive nutrition tracking service 130 for purchasing different kinds of fruits in September.

Figure 22:
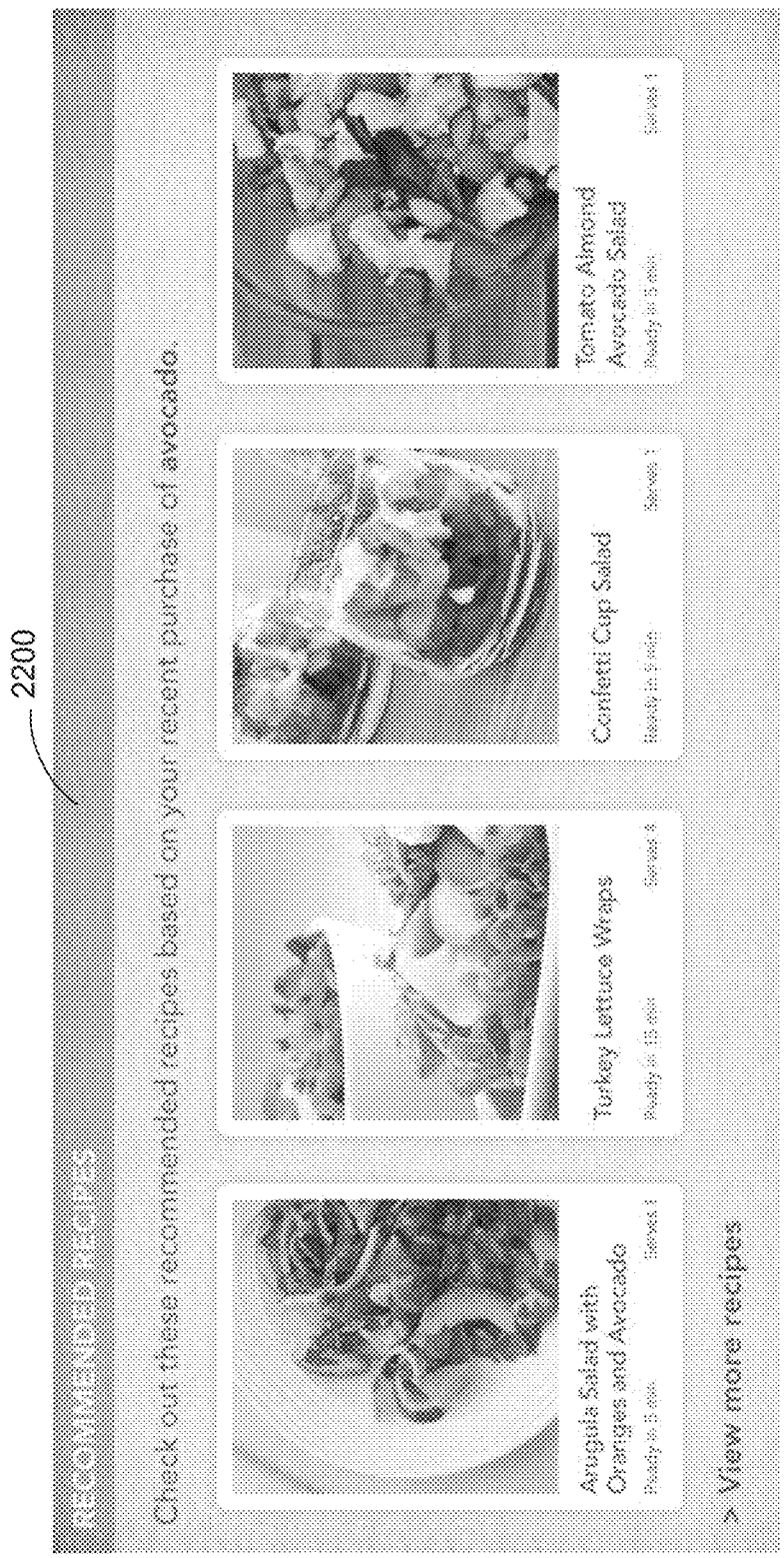
FIG. 22 shows an example of recommended recipes to a user based on passive tracking of the user's recent avocado purchase.
Figure 23:
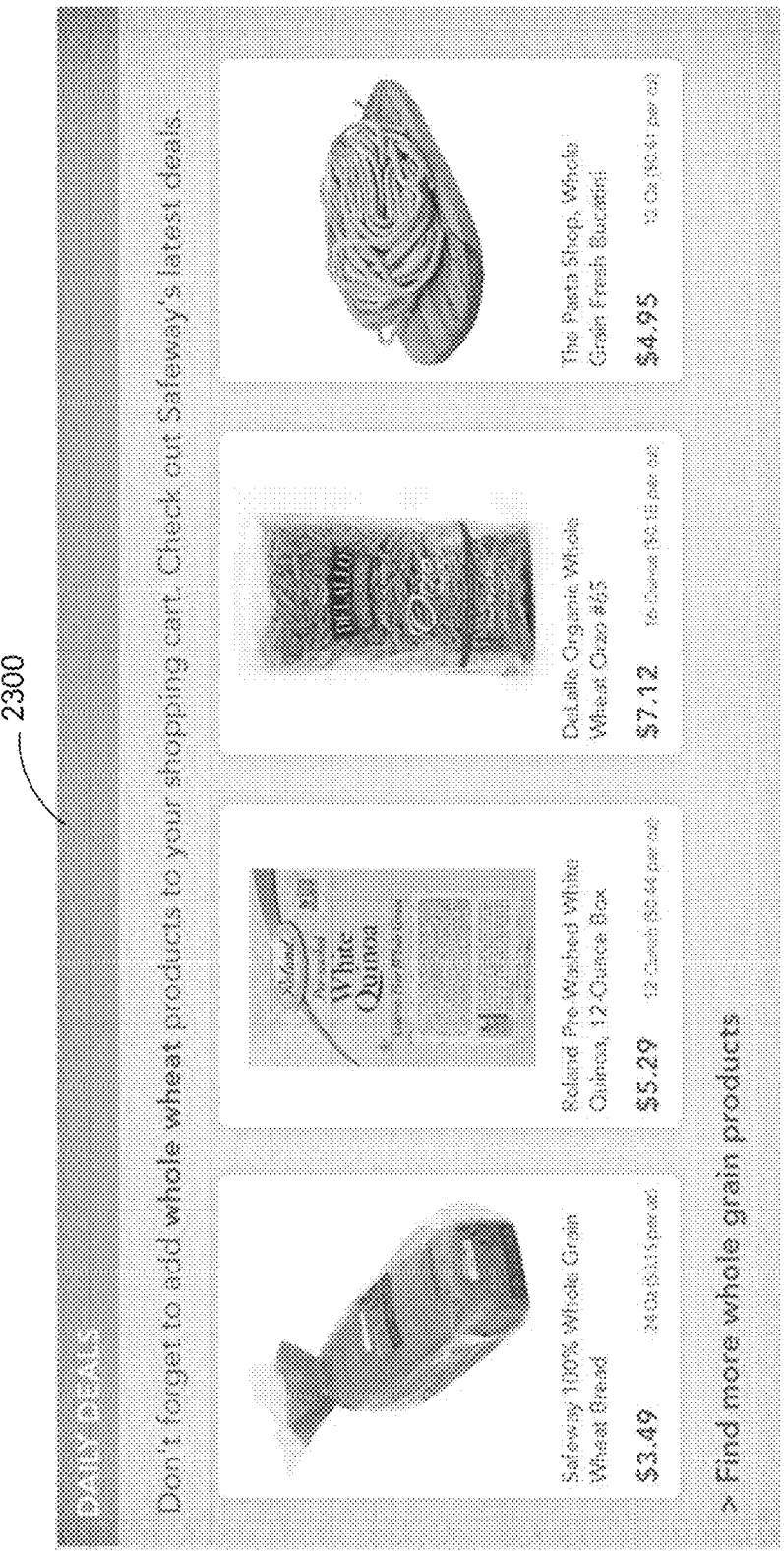
FIG. 23 shows an example of personalized healthy lifestyle recommendations to a user based on passive tracking of the user's calories and nutrients consumption.

FIG. 22 shows an example of recommended recipes 2200 to Kelly based on passive tracking of Kelly's recent avocado purchase. Each of the recommended recipes is tailored for Kelly by including avocado in the recipe. FIG. 23 shows an example of personalized healthy lifestyle recommendations 2300 to Kelly based on passive tracking of Kelly's calories and nutrients consumption. In the example of FIG. 23, the passive nutrition tracking service 130 reminds Kelly to include whole wheat in her diet for balanced nutrition and provides various sources for whole wheat in her diet.

General

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A computer-implemented method comprising:
   receiving loyalty information from a client device of a user of a tracking system, the loyalty information indicating that the user belongs to a loyalty program of a grocery store;
   receiving grocery information from a first computer server associated with the loyalty program, the grocery information describing a first plurality of food items that the user acquired at the grocery store;
   receiving restaurant information from a second computer server associated with a restaurant, the restaurant information describing a second plurality of food items that the user acquired at the restaurant, the restaurant information determined based on dish information programmed onto radio-frequency identification (RFID) tags coupled to receptacles each configured to contain at least one of the food items of the second plurality of food items;
   estimating a third plurality of food items included in a pantry of the user based on average pantry food item consumption according to survey responses of a population of users of the tracking system and a family size of the user;
   determining, using a database table including mappings of food items to numbers of calories, a total number of calories consumed by the user based at least in part on the first plurality of food items, the second plurality of food items, and the third plurality of food items;
   determining an energy expenditure of the user using sensor data from a physical activity tracker of the user and estimates based on activity of the population of users of the tracking system; and
   providing a recommendation based at least in part on the total number of calories consumed by the user and a number of calories used by the user according to the energy expenditure for display on the client device.

2. The computer-implemented method of claim 1, further comprising:
   receiving, from a wireless transceiver, device information of the client device; and
   determining that the user acquired the second plurality of food items in response to determining that the device information is associated with the user.

3. The computer-implemented method of claim 1, further comprising:
   receiving free food consumption information from the client device indicating a fourth plurality of food items, different than the first plurality of food items, the second plurality of food items, and the third plurality of food items consumed by the user; and
   wherein determining the total number of calories consumed by the user is further based on the fourth plurality of food items.

4. The computer-implemented method of claim 1, further comprising:
   determining a nutrient information based on the first plurality of food items, the second plurality of food items, and the third plurality of food items, the nutrient information indicating an intake level of the user of at least one of sodium, fat, and cholesterol during a predetermined period of time; and
   wherein the recommendation is further based on the nutrient information.

5. The computer-implemented method of claim 4, further comprising:
   determining that the intake level of the user is greater than a threshold value based on a recommended daily allowance; and
   wherein the recommendation indicates that the user should reduce the intake level.

6. The computer-implemented method of claim 1, further comprising:
   receiving user information describing demographic data of the user;
   receiving population level norms describing recommended nutrient and caloric intake levels; and
   wherein determining the total number of calories consumed by the user is further based on the demographic data and the population level norms.

7. The computer-implemented method of claim 6, wherein the user information further describes genetic data of the user, and wherein the recommended nutrient and caloric intake levels are associated with other users having similar demographic data or genetic data with the user.

8. The computer-implemented method of claim 1, wherein the population of users of the tracking system shares similar demographic characteristics as the user.

9. A non-transitory computer readable medium storing executable computer program instructions that, when executed by a processor, cause the processor to:
- receive loyalty information from a client device of a user of a tracking system, the loyalty information indicating that the user belongs to a loyalty program of a grocery store;
- receive grocery information from a first computer server associated with the loyalty program, the grocery information describing a first plurality of food items that the user acquired at the grocery store;
- receive restaurant information from a second computer server associated with a restaurant, the restaurant information describing a second plurality of food items that the user acquired at the restaurant, the restaurant information determined based on dish information programmed onto radio-frequency identification (RFID) tags coupled to receptacles each configured to contain at least one of the food items of the second plurality of food items;
- estimating a third plurality of food items included in a pantry of the user based on average pantry food item consumption according to survey responses of a population of users of the tracking system and a family size of the user;
- determine, using a database table including mappings of food items to numbers of calories, a total number of calories consumed by the user based at least in part on the first plurality of food items, the second plurality of food items, and the third plurality of food items;
- determine an energy expenditure of the user using sensor data from a physical activity tracker of the user and estimates based on activity of the population of users of the tracking system; and
- provide a recommendation based at least in part on the total number of calories consumed by the user and a number of calories used by the user according to the energy expenditure for display on the client device.

10. The computer-readable storage medium of claim 9, having further instructions that when executed by the processor cause the processor to:
- receive, from a wireless transceiver, device information of the client device; and
- determine that the user acquired the second plurality of food items in response to determining that the device information is associated with the user.

11. The computer-readable storage medium of claim 9, having further instructions that when executed by the processor cause the processor to:
- receive free food consumption information from the client device indicating a fourth plurality of food items, different than the first plurality of food items, the second plurality of food items, and the third plurality of food items consumed by the user; and
- wherein determining the total number of calories consumed by the user is further based on the fourth plurality of food items.

12. The computer-readable storage medium of claim 9, having further instructions that when executed by the processor cause the processor to:
- determine a nutrient information based on the first plurality of food items, the second plurality of food items, and the third plurality of food items, the nutrient information indicating an intake level of the user of at least one of sodium, fat, and cholesterol during a predetermined period of time; and
- wherein the recommendation is further based on the nutrient information.

13. The computer-readable storage medium of claim 12, having further instructions that when executed by the processor cause the processor to:
- determine that the intake level of the user is greater than a threshold value based on a recommended daily allowance; and
- wherein the recommendation indicates that the user should reduce the intake level.

14. The computer-readable storage medium of claim 9, having further instructions that when executed by the processor cause the processor to:
- receive user information describing demographic data of the user;
- receive population level norms describing recommended nutrient and caloric intake levels; and
- wherein determining the total number of calories consumed by the user is further based on the demographic data and the population level norms.

15. The computer-readable storage medium of claim 14, wherein the user information further describes genetic data of the user, and wherein the recommended nutrient and caloric intake levels are associated with other users having similar demographic data or genetic data with the user.

16. The computer-readable storage medium of claim 9, wherein the population of users of the tracking system shares similar demographic characteristics as the user.

17. A method comprising:
- receiving loyalty information from a client device of a user of a tracking system, the loyalty information indicating that the user belongs to a loyalty program of a grocery store;
- receiving grocery information from a first computer server associated with the loyalty program, the grocery information describing a first plurality of food items that the user acquired at the grocery store;
- receiving restaurant information from a second computer server associated with a restaurant, the restaurant information describing a second plurality of food items that the user acquired at the restaurant, the restaurant information determined based on dish information programmed onto radio-frequency identification (RFID) tags coupled to receptacles each configured to contain at least one of the food items of the second plurality of food items;
- estimating a third plurality of food items included in a pantry of the user based on average pantry food item consumption according to survey responses of a population of users of the tracking system and a family size of the user;
- determining, using a database table including mappings of food items to numbers of calories, a total number of calories consumed by the user based on the first plurality of food items, the second plurality of food items, and the third plurality of food items;
- determining an energy expenditure of the user using sensor data from a physical activity tracker of the user and estimates based on activity of the population of users of the tracking system;
- predicting a daily intake of a plurality of nutrients of the user based on a correlation with the total number of calories and a number of calories used by the user according to the energy expenditure;
- modifying a dietary history of the user based on the total number of calories and the predicted daily intake of the plurality of nutrients; and providing a customized health feedback generated based on the dietary history to the client device for display to the user.

18. The method of claim 17, further comprising:

receiving free food consumption information from the client device indicating a fourth plurality of food items, different than the first plurality of food items, the second plurality of food items, and the third plurality of food items consumed by the user; and wherein determining the total number of calories consumed by the user is further based on the fourth plurality of food items.

19. The system of claim 17, wherein the dietary history of the user indicates that a daily intake of a nutrient of the plurality of nutrients is lower than a threshold value, and wherein the customized health feedback includes a recommendation indicating that the user should consume a greater amount of the nutrient.

20. The method of claim 17, wherein the population of users of the tracking system shares similar demographic characteristics as the user.

\* \* \* \* \*

UNITED STATES PATENT AND TRADEMARK OFFICE
CERTIFICATE OF CORRECTION

PATENT NO. : 10,049,598 B1
APPLICATION NO. : 14/514287
DATED : August 14, 2018
INVENTOR(S) : Langheier et al.

Page 1 of 1

It is certified that error appears in the above-identified patent and that said Letters Patent is hereby corrected as shown below:

In the Claims

Column 19, Line 13, after "The" delete "system" and insert -- method --.

Signed and Sealed this
Fifth Day of March, 2019

Andrei Iancu
*Director of the United States Patent and Trademark Office*